United States Patent [19]

Rasberger

[11] 4,198,334

[45] Apr. 15, 1980

[54] SUBSTITUTED MALONIC ACID DERIVATIVES AND THEIR USE AS STABILIZERS

[75] Inventor: Michael Rasberger, Riehen, Switzerland

[73] Assignee: Ciba-Geigy Corporation, Ardsley, N.Y.

[21] Appl. No.: 861,090

[22] Filed: Dec. 15, 1977

Related U.S. Application Data

[63] Continuation-in-part of Ser. No. 738,992, Nov. 4, 1976, abandoned.

[30] Foreign Application Priority Data

| Nov. 7, 1975 | [CH] | Switzerland | 14432/75 |
| Nov. 7, 1975 | [CH] | Switzerland | 14433/75 |
| Apr. 2, 1976 | [CH] | Switzerland | 4146/76 |
| Apr. 2, 1976 | [CH] | Switzerland | 4147/76 |
| Sep. 3, 1976 | [CH] | Switzerland | 11214/76 |

[51] Int. Cl.$^2$ .................. C07D 401/12; C08K 5/34
[52] U.S. Cl. ....................... 260/45.8 N; 106/176; 252/403; 260/45.85 B; 546/16; 546/188; 546/190
[58] Field of Search ............. 260/45.8 NP, 293.64, 260/293.63; 546/188, 190, 16

[56] References Cited

U.S. PATENT DOCUMENTS

| 3,993,655 | 11/1976 | Rasberger et al. | 260/293.64 |
| 4,021,432 | 5/1977 | Holt et al. | 260/293.63 |

*Primary Examiner*—Hosea E. Taylor
*Assistant Examiner*—R. A. White
*Attorney, Agent, or Firm*—Wenderoth, Lind & Ponack

[57] ABSTRACT

Esters and amides from 4-hydroxy-and 4-aminopolyalkylpiperidines and hydroxybenzylmalonic acids substituted at the central carbon atom with an organic residue, preferably alkyl-, esteralkyl- or phosphonoalkyl-groups, are excellent stabilizers for organic polymers, especially for polyolefins. They protect the polymers as well against light degradation as against thermo-oxidative degradation. The compounds can be prepared by hydroxybenzylation of the corresponding derivatives of substituted malonic acids. Bis-malonic acid derivatives may be obtained from the monomalonics by reaction with formaldehyde.

21 Claims, No Drawings

SUBSTITUTED MALONIC ACID DERIVATIVES AND THEIR USE AS STABILIZERS

This application is a continuation-in-part of copending application Ser. No. 738,992, filed Nov. 4, 1976 (now abandoned).

The invention relates to new esters of hydroxybenzylmalonic acids, to their manufacture and to their use as stabilisers for plastics, as well as to the material stabilised therewith.

The compounds concerned are those of the formula I

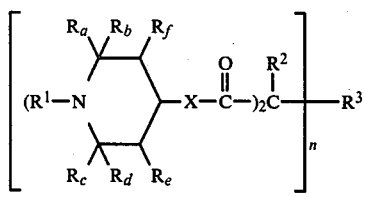

and the acid addition salts thereof, wherein n is 1 or 2, $R_a$ represents alkyl having 1-6 carbon atoms, $R_b$ represents alkyl having 1-6 carbon atoms, $R_c$ represents alkyl having 1-9 carbon atoms, phenyl, benzyl or phenylethyl, $R_d$ represents alkyl having 1-6 carbon atoms, or $R_c$ and $R_d$ together represent tetra- or pentamethylene, $R_e$ represents hydrogen, alkyl having 1-5 carbon atoms, alkenyl or alkynyl having 3-4 carbon atoms or aralkyl having 7-8 carbon atoms, $R_f$ represents hydrogen, alkyl having 1-5 carbon atoms, alkenyl or alkynyl having 3-4 carbon atoms, or aralkyl having 7-8 carbon atoms, with $R_e$ and $R_f$ being mutually exchangeable, and X represents oxygen or —NR—, R represents hydrogen, alkyl having 1-18 carbon atoms, alkenyl having 3-4 carbon atoms, alkynyl having 3-4 carbon atoms, cycloalkyl having 5-12 carbon atoms, aryl having 6-10 carbon atoms, or aralkyl having 7-9 carbon atoms, $R_1$ represents hydrogen, —O·, —OH, alkyl having 1-12 carbon atoms, alkenyl having 3 or 4 carbon atoms, propargyl, benzyl or a group of the formula —CH$_2$—CH(OR$^5$)—R$^4$ wherein R$^4$ represents hydrogen, methyl or phenyl and R$^5$ represents hydrogen or a group A—CO—, or R$^1$ represents a group A—CO—, and in both cases A represents alkyl having 1-12 carbon atoms, alkenyl having 2 or 3 carbon atoms, cyclohexyl, phenyl, benzyl, a phenyl or phenylethyl group substituted by 2 alkyl groups each having 1-4 carbon atoms and a hydroxyl group, alkylamino having 1-12 carbon atoms, dialkylamino having 2-16 carbon atoms, anilino, alkoxy having 1-12 carbon atoms, benzyloxy or phenoxy, R$^2$ represents a hydroxybenzyl group of the formula II

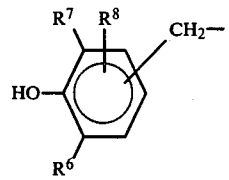

wherein R$^6$ and R$^7$ each independently represent an alkyl group having 1-9 carbon atoms, aralkyl having 7-9 carbon atoms or cycloalkyl having 5-8 carbon atoms, and R$^8$ represents hydrogen or methyl, and R$_3$ represents, in the case where n is 1, alkyl having 1-20 carbon atoms, or alkyl having 1-10 carbon atoms which is substituted by one or more of the groups —OR$^9$, —SR$^{10}$, —CO—R$^{11}$, —CN, —C(O)—YR$^{12}$, —O—C(O)R$^{13}$ or —P(O)(OR$^{14}$)$_2$, wherein R$^9$ denotes phenyl or alkylphenyl having 7-10 carbon atoms, benzyl or cyclohexyl, R$^{10}$ denotes phenyl or alkylphenyl having 7-10 carbon atoms, R$^{11}$ denotes alkyl having 1-12 carbon atoms, Y denotes oxygen or —NR—, whereby R has the above-given meaning, R$^{12}$ denotes alkyl having 1-18 carbon atoms, cycloalkyl having 5-12 carbon atoms, or a group of the formula III

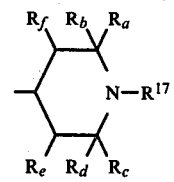

wherein R$^{17}$ has one of the meanings given for R$^1$, R$^{13}$ denotes alkyl having 1-17 carbon atoms, cycloalkyl having 5-12 carbon atoms, or phenyl or phenylalkyl having 7-9 carbon atoms, whereby the phenyl radical can be substituted by alkyl having 1-4 carbon atoms and/or hydroxyl, and R$^{14}$ denotes alkyl having 1-8 carbon atoms, allyl or phenyl, and X has the above-defined meaning, and R$^3$ further represents an alkyl group having 2-22 carbon atoms which is interrupted by —O—, —S—, —SO— or —SO$_2$—, alkenyl having 3-18 carbon atoms, alkynyl having 3-8 carbon atoms, cycloalkyl having 5-12 carbon atoms, alkyl-cycloalkyl having 6-18 carbon atoms, cycloalkyl-alkyl having 6-14 carbon atoms, aralkyl or alkyl-aralkyl having 7-19 carbon atoms, phenyl or a group —OR$^{15}$, whereby R$^{15}$ can be alkyl having 1-18 carbon atoms, alkenyl having 3-4 carbon atoms, alkynyl having 3-4 carbon atoms, cycloalkyl having 5-12 carbon atoms or aralkyl having 7-9 carbon atoms, or R$^3$ represents a group —O—C(O)R$^{16}$ or —NH—C(O)R$^{16}$, whereby R$^{16}$ can be alkyl having 1-12 carbon atoms, alkenyl having 2 or 3 carbon atoms, cyclohexyl, phenyl, benzyl, a phenyl or phenylethyl group substituted by 2 alkyl groups each having 1-4 carbon atoms and a hydroxyl group, or R$^3$ is a group of the formula III or of the formula IV

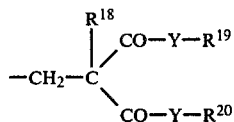

wherein $R^{18}$ represents alkyl having 1–20 carbon atoms, allyl, benzyl, phenyl, cyclohexyl, alkoxyalkyl having 3–8 carbon atoms, or a group —O—C(O)$R^{16}$ or —NH—C(O)$R^{16}$ as defined above, or has one of the meanings given for $R^2$, and $R^{19}$ and $R^{20}$ each independently represent alkyl having 1–6 carbon atoms, or a radical of the formula III, and, in addition, $R_3$ represents, in the case where n is 2, a direct bond, alkylene having 1–20 carbon atoms, alkylene having 2–20 carbon atoms which is interrupted by one or two of the members —O—, —S—, —SO—, —$SO_2$— or —CO—O—, arylene-bis-alkylene having 8–14 carbon atoms, alkylene having 4–8 carbon atoms or alkynylene having 4–8 carbon atoms.

$R_a$, $R_b$ and $R_d$ can be straight-chain or branched-chain alkyl groups having 1–6 carbon atoms, such as methyl, ethyl, propyl, butyl, isobutyl, isopentyl or n-hexyl.

$R_c$ can be a straight-chain or branched-chain alkyl group having 1–9 carbon atoms, such as methyl, ethyl, propyl, n-butyl, isobutyl, isopentyl, n-hexyl, 2-ethylhexyl, n-nonyl or isononyl.

$R_e$ and $R_f$ can be alkyl groups having up to 5 carbon atoms, with $R_e$ preferably containing 1 carbon atom less than $R_b$ and the position of $R_e$ and $R_f$ being exchangeable. $R_e$ and $R_f$ can also represent alkenyl or alkynyl, for example allyl, methallyl, 2-butenyl or propargyl, especially allyl. $R_e$ and $R_f$ can also represent aralkyl, for example benzyl, phenylethyl or methylbenzyl, preferably benzyl.

Preferably $R_a$, $R_b$, $R_c$ and $R_d$ are methyl, and $R_e$ and $R_f$ are hydrogen.

$R^1$, $R^{16}$ and A as an alkyl group having 1–12 carbon atoms can be a primary alkyl group, such as a methyl, ethyl, n-propyl, n-butyl, n-hexyl, n-octyl, n-decyl or n-dodecyl group.

R and $R^{15}$ as alkyl having up to 18 carbon atoms can in addition be; e.g., tridecyl, hexadecyl or octadecyl.

R, $R^1$, $R^{15}$, $R^{16}$ and A as an alkenyl group can be, e.g., an allyl, methallyl or butenyl group.

R and $R^{15}$ as alkynyl having 3–4 carbon atoms can be, e.g., propargyl or methylpropargyl.

R and $R^{15}$ as cycloalkyl having 5–12 carbon atoms can be, e.g., cyclopentyl, cyclohexyl, cyclooctyl or cyclododecyl.

R as aryl can be, for example, phenyl, tolyl or naphthyl.

R and $R^{15}$ as aralkyl can be, e.g., benzyl, phenylethyl or phenylpropyl.

If $R^1$ and/or $R^5$ represent a group A—CO—, then this can be, depending on the meaning of A, a carbonic acid radical such as acetyl, propionyl, butyryl, capronyl, caprylol, lauroyl, acryloyl, crotonoyl, phenylacetyl, β-(3,5-di-tert. butyl-4-hydroxyphenyl)-propionyl or benzoyl; or a carbamoyl radical such as methylcarbamoyl, butylcarbamoyl, dodecylcarbamoyl, diethylcarbamoyl, dihexylcarbamoyl, dioctylcarbamoyl or phenylcarbamoyl; or a carbonic ester radical such as ethoxycarbonyl, isopropoxycarbonyl, 2-ethylhexyloxycarbonyl, dodecyloxycarbonyl, benzyloxycarbonyl or phenoxycarbonyl.

According to its definition by formula II, $R^2$ can be a para- or meta-hydroxybenzyl group. The substituents $R^6$ and $R^7$ on the benzyl radical can be straight-chain or branched-chain alkyl groups having 1–9 carbon atoms, e.g. methyl, ethyl, isopropyl, tert.butyl, n-hexyl, 1,1,3,3-tetramethylbutyl or tert.nonyl. In the case where $R^6$ or $R^7$ represent cycloalkyl, this can be, for example, cyclopentyl, methylcyclopentyl, cyclohexyl or methylcyclohexyl. Where $R^6$ or $R^7$ represents aralkyl, this can be, e.g., benzyl or α,α-dimethylbenzyl. $R^6$ and $R^7$ are preferably alkyl groups having 1–4 carbon atoms, especially methyl or tert.butyl.

Depending on the value of n, $R^3$ can be a mono- or bivalent organic radical. As alkyl having 1–20 carbon atoms, $R^3$ can be, e.g., one of the alkyl groups given above for $R^1$; it can also represent branched-chain alkyl such as isopropyl, isopentyl, 2-ethylbutyl, 2-ethylhexyl or isononyl, or higher alkyl radicals such as n-hexadecyl, n-octadecyl or n-eicosyl.

As a substituted or interrupted alkyl group, $R^3$ can be, for example, one of the following radicals: 2-phenoxyethyl, 2-benzyloxyethyl, 2-p-tolyloxypropyl, cyclohexyloxymethyl, 2,3-di(phenoxy)propyl, 2-phenylthioethyl, 2-(4-tert.butylphenylthio)-ethyl, 2-acetylethyl, 2-isobutyrylethyl, 2-(dodecylcarbonyl)-ethyl, 2-cyanoethyl, cyanomethyl, 3-cyanopropyl, methoxycarbonylmethyl, dodecyloxycarbonylmethyl, 2-ethoxycarbonylethyl, 1,2-di(methoxycarbonyl) ethyl, 2,3-di(ethoxycarbonyl)propyl, 2-(butylaminocarbonyl) ethyl, 2-(cyclohexyloxycarbonyl)-ethyl, 2-(tert.butyloxycarbonyl)-ethyl, 2-(octadecyloxycarbonyl)-propyl, 4-(propoxycarbonyl)-butyl, 2-acetoxyethyl, 1,2-diacetoxy-ethyl, 2-(isooctanoyloxy)-propyl, 2-(octadecanoyloxy)-ethyl, 2-(cyclopentylcarbonyloxy)-ethyl, 3-benzoyloxypropyl, 2-(p-tert.butylbenzoyloxy)-ethyl, 2-salicyloyloxy-ethyl, 2-(3,5-di-tert.butyl-4-hydroxybenzoyloxy)-ethyl, 2-phenylacetyloxyethyl, 2-(3,5-di-tert.butyl-4-hydroxyphenylpropionyloxy)-propyl, diethylphosphonomethyl, 2-dimethylphosphono-ethyl, 2-(dioctylphosphono)-ethyl, diphenylphosphonomethyl, 3-(diallylphosphono)-propyl, methoxymethyl, 2-butoxyethyl, 2-octadecyloxyethyl, isopropoxymethyl, 3-butylthio-propyl, 2-dodecylthioethyl, 2-(isohexylsulphinyl)-ethyl, 2-octadecylsulphonyl-ethyl, 2-ethylsulphonyl-propyl, 2-(2,2,6,6-tetramethylpiperidin-4-yloxycarbonyl)-ethyl, 2-(1,2,2,6,6-pentamethylpiperidin-4-ylaminocarbonyl)-ethyl, 2-(2,2,6,6-tetramethylpiperidin-4-yloxycarbonyl)-2-(methoxycarbonyl)-hexyl or 2,2-bis-(2,2,6,6-tetramethylpiperidin-4-ylaminocarbonyl)-hexyl.

As an alkenyl or alkynyl group, $R^3$ can be, for example, allyl, methallyl, 2-buten-1-yl, 3-hexen-1-yl, undecenyl, oleyl, propargyl or 2-heptyn-1-yl.

Examples of $R^3$ as cycloalkyl, alkyl-cycloalkyl or cycloalkyl-alkyl are the radicals cyclopentyl, cyclohexyl, cyclooctyl, cyclododecyl, methylcyclopentyl, dimethylcyclohexyl, propylcyclooctyl, hexylcyclododecyl, cyclohexylmethyl, 3-cyclooctylpropyl or decahydronaphthyl-α-methyl.

Examples of $R^3$ as aralkyl or alkyl-aralkyl are the groups benzyl, 2-phenylethyl, 2-phenylpropyl, β-naphthylmethyl, 4-methylbenzyl, 4-t-butylbenzyl or 4-methylnaphthyl-1-methyl.

$R^3$ as a group —O—CO—$R^{16}$ or —NH—CO—$R^{16}$ can be, for example, acetoxy, propionoxy, butyroxy, octanoyloxy, dodecanoyloxy, acryloxy, crotonoxy, benzoyloxy, phenylacetoxy, 3,5-di-tert.butyl-4-hydroxybenzoyloxy, acetamino, butyrylamino, decanoylamino, acroylamino, benzoylamino or cyclohexylcarbonylamino.

In the case where n is 2, $R^3$ represents a direct bond or a bivalent organic radical. This can be alkylene, e.g. methylene, ethylene or polymethylene having up to 20 carbon atoms; or the alkylene radical is interrupted by 1 or 2 hetero members, such as the bivalent radicals, $-CH_2O-CH_2-$, $-CH_2CH_2O-CH_2CH_2-$, $-CH_2CH_2-O-CH_2CH_2-O-CH_2CH_2-$, $-(CH_2)_3-S-(CH_2)_3-$, $-CH_2CH_2-S-(CH_2)_4-S-CH_2CH_2-$, $-CH_2CH_2-SO-CH_2CH_2-$, $-CH_2CH_2-SO_2-CH_2-CH_2CH_2-$, $-CH_2CH_2-SO_2-(CH_2)_8-SO_2-CH_2CH_2-$, $-CH_2COOCH_2CH_2OOCCH_2-$, $-CH_2CH_2COOCH_2CH_2OOCCH_2CH_2-$, $-CH_2CH_2-COO(CH_2)_4-OOC-CH_2CH_2-$, $-CH_2CH_2OCO(CH_2)_4COOCH_2CH_2-$ and $-CH_2CH_2OCO(CH_2)_8COOCH_2CH_2-$. $R^3$ can also be arylene-bis-alkylene, e.g. p-xylylene, benzene-1,3-bis(ethylene), diphenyl-4,4'-bis(methylene) or naphthalene-1,4-bis(methylene). It can, finally, be alkenylene or alkynylene having 4–8 carbon atoms, such as 2-butenylene-1,4, 2-butynylene-1,4 or 2,4-hexadiynylene-1,6.

The compounds of the formula I impart to plastics excellent protection against thermal-oxidative ageing, such as light-induced ageing. It is known that plastics can be stabilised by the addition of antioxidants or of light stabilisers or of a mixture of both, in consequence of which their service life is considerably lengthened. There have recently become known also stabilisers which simultaneously have an antioxidative and light-stabilising action. In DT-OS No. 2,456,864 there have thus been described 4-piperidinol esters of mono- and di-(hydroxybenzyl)-malonic acids which have a stabilising action that is greater than that of a corresponding mixture of a hydroxybenzylmalonate, known as an antioxidant, and a 4-piperidinol derivative, known as a light stabiliser. If in the compounds of DT-OS No. 2,456,864 a hydroxybenzyl radical or a hydrogen atom is replaced by an alkyl group or by another group known as being inactive (such as one that has just been defined as $R^3$), then there is surprisingly obtained an increase in the antioxidative and light-stabilising effectiveness. Some compounds of the formula I surpass in effectiveness in certain plastics all stabilisers at present known, so that the invention is therefore of great importance for the technology of plastics.

Preferred compounds of formula I are those wherein $R_a$ to $R_d$ are methyl, and $R_e$ and $R_f$ are hydrogen, or wherein $R_a$ and $R_c$ are ethyl, $R_b$, $R_d$ and $R_e$ are methyl, and $R_f$ is hydrogen. Also preferred are compounds of formula I wherein X is oxygen or NH, $R^1$ is hydrogen, $-O\cdot$, $-OH$, alkyl having 1–4 carbon atoms, allyl, propargyl, acetyl, acryloyl or crotonoyl, $R^2$ represents a hydroxybenzyl group of the formula IIa or IIb,

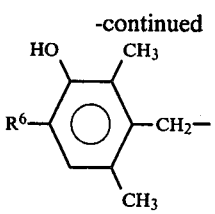

(IIa)

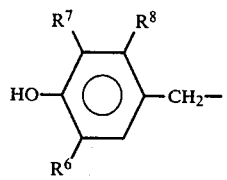

(IIb), $R^6$ and $R^7$ each independently represent alkyl having 1 to 4 carbon atoms, $R^8$ represents hydrogen or methyl, $R^3$ represents in the case where n is 1 alkyl having 1–18 carbon atoms, alkyl having 1–4 carbon atoms which is substituted by one or two of the groups $-CN$, $-C(O)-YR^{12}$, $-O-C(O)R^{13}$ or $-P(O)(OR^{14})_2$, wherein Y is $-O-$ or $-NH-$, $R^{12}$ can be alkyl having 1–4 carbon atoms, or a group of the formula IIIb

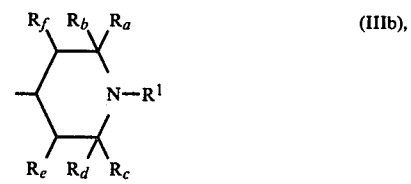

(IIIb), $R^{13}$ can be alkyl having 1–17 carbon atoms, cyclohexyl, phenyl or benzyl, and $R^{14}$ can be alkyl having 1–4 carbon atoms or allyl, and $R^3$ further represents alkyl having 2–18 carbon atoms which is interrupted by $-O-$ or $-S-$, cycloalkyl having 5–12 carbon atoms, alkylcycloalkyl having 6–18 carbon atoms, alkenyl having 3–6 carbon atoms, alkynyl having 3–6 carbon atoms, phenyl, aralkyl having 7–15 carbon atoms, or a group $-OR^{15}$, wherein $R^{15}$ represents alkyl having 1–12 carbon atoms, allyl, propargyl or benzyl, or a group $-O-COR^{16}$ or $-NH-COR^{16}$, wherein $R^{16}$ represents alkyl having 1–12 carbon atoms, phenyl, 3,5-di-tert.butyl-4-hydroxyphenyl or 2-(3,5-di-tert.butyl-4-hydroxyphenyl)-ethyl, or a group of the formula IIIb, or in the case where n is 2
a direct bond, alkylene having 1–12 carbon atoms which can be interrupted by one or two of the groups $-O-$, $-S-$ or $-CO-O-$, arylene-bis-alkylene having 8–14 carbon atoms or alkylene having 4–8 carbon atoms.

Particularly preferred are compounds of the formula I wherein n is 1 or 2, $R_a$, $R_b$, $R_c$ and $R_d$ are methyl, and $R_e$ and $R_f$ are hydrogen, X is oxygen, $R^1$ is hydrogen, $-O\cdot$, alkyl having 1–4 carbon atoms, allyl or acetyl, $R^2$ is a hydroxybenzyl group of the formula IIa or IIb wherein $R^6$ represents tert. butyl, $R^7$ represents methyl or tert.butyl and $R^8$ represents hydrogen or methyl, and $R^3$ represents alkyl having 1–18 carbon atoms, which is substituted by 1 or 2 groups $-C(O)-OR^{12}$, wherein $R^{12}$ represents alkyl having 1–4 carbon atoms or a group of the formula IIIa

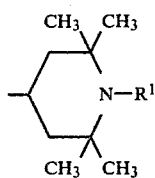

(IIIa), or is substituted by a group —P(O)(OR$^{14}$)$_2$, wherein R$^{14}$ represents alkyl having 1–4 carbon atoms, or R$^3$ represents allyl, propargyl, benzyl, phenyl, alkylene having 1–8 carbon atoms or xylylene.

The present invention embraces also the salts of compounds of the formula I, which are formed by the addition of acids in amounts at most equivalent to the piperidine groups. Such acids can be inorganic acids such as sulphuric, hydrochloric or phosphoric acid, organic carboxylic acids such as formic, acetic, oxalic, maleic, benzoic or salicylic acid, organic sulphonic acids such as methane- or p-toluenesulphonic acid, or organic phosphorus-containing acids such as diphenylphosphoric acid, methanephosphonic acid or diphenylphosphinic acid.

Examples of compounds of the formula I are:

butyl-(3,5-di-tert.butyl-4-hydroxybenzyl)-malonic acid-bis-(2,2,6,6-tetramethyl-4-piperidinyl)ester, allyl-(3,5-di-tert.butyl-4-hydroxybenzyl)-malonic acid-bis(1-allyl-2,2,6,6-tetramethyl-4-piperidinyl)ester, ethyl-(3,5-di-tert.butyl-4-hydroxybenzyl)-malonic acid-bis(1-hydroxyl-2,2,6,6-tetramethyl-4-piperidinyl)ester, propargyl-(3,5-di-tert.butyl-4-hydroxybenzyl)-malonic acid-bis(1,2,2,6,6-pentamethyl-4-piperidinyl)ester, β-methoxyethyl-(3-methyl-5-α,α-dimethylbenzyl-4-hydroxybenzyl)malonic acid-bis(2,2,6,6-tetramethyl-4-piperidinyl)ester, dodecyl-(2,6-dimethyl-4-tert.butyl-3-hydroxybenzyl)-malonic acid-bis(1-acryl-2,2,6,6-tetramethyl-4-piperidinyl)ester, phenylthiomethyl-(3-tert.butyl-5-tert.amyl-4-hydroxybenzyl)malonic acid-bis(1-acetyl-2,2,6,6tetramethyl-4-piperidinyl)ester, ester, dodecylthioethyl-(3-methyl-5-cyclohexyl-4-hydroxybenzyl)-malonic acid-bis(1,2,2,6,6-pentamethyl-4-piperidinyl)ester, dodecylsulphonylethyl-(3-methyl-5-cyclohexyl-4-hydroxybenzyl)-malonic acid-bis(1,2,2,6,6-pentamethyl-4-piperidinyl)ester, methyloxycarbonylmethyl-(3,5-di-tert.butyl-4-hydroxybenzyl)-malonic acid-bis(1-oxyl-2,2,6,6-tetramethyl-4-piperidinyl)ester, γ-octyloxypropyl-(3-methyl-5-ditert.octyl-4-hydroxybenzyl)-malonic acid-bis(1-crotonyl-2,2,6,6-tetramethyl-4-piperidinyl)ester, β-butylcarbonylethyl-(3,5-di-tert.butyl-4-hydroxybenzyl)-malonic acid-bis(1-formyl-2,2,6,6-tetramethyl-4-piperidinyl) ester, phenylsulphinylmethyl-(3,5-di-tert.butyl-4-hydroxybenzyl)-malonic acid-bis(1-hydroxy-2,2,6,6-tetramethyl-4-piperidinyl) ester, β-(octyloxycarbonyl)ethyl-(3,5-di-tert.butyl-4-hydroxybenzyl)-malonic acid-bis(1-propyl-2,2,6,6-tetramethyl-5-piperidinyl) ester, 1,2,2,6,6-pentamethyl-4-piperidineoxycarbonylmethyl-(3,5-di-tert.butyl-4-hydroxybenzyl)-malonic acid-bis(1,2,2,6,6-pentamethyl-4-piperidinyl)ester, benzyl-(3-methyl-5-ditert.octyl-4-hydroxybenzyl)-malonic acid-bis(2,2,6,6-tetramethyl-4-piperidinyl)ester, cyclohexyl-(2,3-dimethyl-5-tert.butyl-4-hydroxybenzyl)-malonic acid-bis(2,2,6,6-tetramethyl-4-piperidinyl)ester, 2,2,6,6-tetramethyl-4-piperidinyl-(3,5-di-tert.butyl-4-hydroxybenzyl)-malonic acid-bis-(1,2,2,6,6-pentamethyl-4-piperidinyl) ester, β-cyanoethyl-(3-isopropyl-5-tert.butyl-4-hydroxybenzyl)-malonic acid-bis(2,2,6,6-tetramethyl-4-piperidinyl)ester, β-diethylphosphonoethyl-(3,5-di-tert.butyl-4-hydroxybenzyl)-malonic acid-bis(2,2,6,6-tetramethyl-4-piperidinyl)ester, β-diphenylphosphonoethyl-(3,5-di-tert.butyl-4-hydroxybenzyl)-malonic acid-bis(1-benzyl-2,2,6,6-tetramethyl-4-piperidinyl) ester, 1,4-di(3,5-di-tert.butyl-4-hydroxyphenyl)-2,2,3,3-tetra-(1,2,2,6,6-pentamethyl-4-piperidinyloxycarbonyl)-butane, 4,4'-di(3,5-di-tert.butyl-4-hydroxyphenyl)-3,3,3',3'-tetra-(2,2,6,6-tetramethyl-4-piperidinyloxycarbonyl)-dibutylsulphone, 4,4'-di(3,5-di-tert.butyl-4-hydroxyphenyl)-3,3,3',3'-tetra-(2,2,6,6-tetramethyl-4-piperidinyloxycarbonyl)-dibutyl ether, 3,3'-di(3,5-di-tert.butyl-4-hydroxyphenyl)-2,2,2',2'-tetra-(1-acetyl-2,2,6,6-tetramethyl-4-piperidinyloxycarbonyl)-p-dipropylbenzene, 1,8-di(3,5-di-tert.butyl-4-hydroxyphenyl)-2,2',7',7'-tetra-(1,2,2,6,6-pentamethyl-4-piperidinyloxycarbonyl)-oct-4-ene, ethylene-di[δ-3,5-di-tert.butyl-4-hydroxyphenyl-γ-γ-bis(2,2,6,6-tetramethyl-4-piperidinyloxycarbonyl)-valerianate], 1,16-bis(3,5-di-tert.butyl-4-hydroxyphenyl)-2,2,15,15-tetra-kis(1-oxyl-2,2,6,6-tetramethyl-4-piperidinyloxycarbonyl)-hexadecane, 1,8-bis(3-methyl-5-tert.butyl-4-hydroxyphenyl)-2,2,7,7-tetra-kis(1-acetyl-2,2,6,6-tetramethyl-4-piperidinyloxycarbonyl)-oct-4-ine.

butyl-(3,5-di-tert.butyl-4-hydroxybenzyl)-malonic acid-bis (2,6-diethyl-2,5,6-trimethyl-4-piperidinyl)ester, allyl-(3,5-di-tert.butyl-4-hydroxybenzyl)-malonic acid-bis (2,6-diethyl-2,5,6-trimethyl-4-piperidinyl)ester, propargyl-(3,5-di-tert.butyl-4-hydroxybenzyl)-malonic acid-bis(2,6-diethyl-1,2,5,6-tetramethyl-4-piperidinyl)ester, dodecyl-(2,6-dimethyl-4-tert.butyl-3-hydroxybenzyl)-malonic acid-bis(1-acryl-2,6-diethyl-2,5,6-trimethyl-4-piperidinyl) ester, dodecylsulphonylethyl-(3-methyl-5-cyclohexyl-4-hydroxybenzyl)-malonic acid-bis(2,6-diethyl-1,2,5,6-tetramethyl-4-piperidinyl) ester, methyloxycarbonylmethyl-(3,5-di-tert.butyl-4-hydroxybenzyl)-malonic acid-bis(1-oxyl-2,6-diethyl-2,5,6-trimethyl-4-piperidinyl)ester, β-(octyloxycarbonyl)ethyl-(3,5-di-tert.butyl-4-hydroxybenzyl)-malonic acid-bis(1,2,6-tripropyl-2,6-dimethyl-5-ethyl-4-piperidinyl)ester, benzyl-(3-methyl-5-di-tert.octyl-4-hydroxybenzyl)-malonic acid-bis(2,6-diethyl-2,5,6-trimethyl-4-piperidinyl)ester, cyclohexyl-(2,3-dimethyl-5-tert.butyl-4-hydroxybenzyl)-malonic acid-bis(2,6-diethyl-1,2,5,6--tetramethyl-4-piperidinyl)ester, 2,2,6,6-tetramethyl-4-piperidinyl-(3,5-di-tert.butyl-4-hydroxybenzyl)-malonic acid-bis(2,6-diethyl-1,2,5,6-tetramethyl-4-piperidinyl)ester, β-cyanoethyl-(3-isopropyl-5-tert.butyl-4-hydroxybenzyl)-malonic acid-bis(2,5,6,6-tetramethyl-2-ethyl-4-piperidinyl) ester, β-diethylphosphonoethyl-(3,5-di-tert.butyl-4-hydroxybenzyl)-malonic acid-bis(2,6-diethyl-2,5,6-trimethyl-4-piperidinyl) ester, 1,4-di(3,5-di-tert.butyl-4-hydroxyphenyl)-2,2,3,3-tetra-(2,5,6-trimethyl-2,6-diethyl-4-piperidinyloxycarbonyl)-butane.

The compounds of the formula I can be manufactured by various methods which consist of several separate steps in varying sequence. The individual steps consist of reactions that are known, particularly such reactions known from the chemistry of malonic acid derivatives.

Synthesis can commence with conversion of a malonic acid lower alkyl ester such as diethylmalonate, by reaction with a 4-piperidinol or 4-aminopiperidine of the formula V, into the corresponding bis-piperidinyl malonic acid derivative VI.

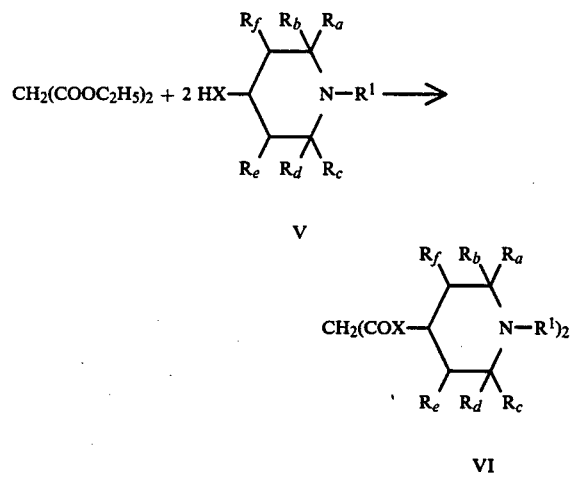

$R^1$ can already be the substituent desired in the compound of the formula I; or the piperidine derivative (V, $R^1$=H) unsubstituted on the nitrogen atom is used and the substituent $R^1$ is introduced after the above reaction, or at a later stage in the course of synthesis.

The introduction of $R^1$ can be effected by the usual methods for N-alkylation or N-acylation; for example by reaction with alkyl halides, alkenyl halides, propargyl chloride, benzyl chloride or carboxylic acid chlorides, preferably in the presence of molar amounts of a base. Hydroxyalkyl radicals are introduced by reaction with epoxides, for example ethylene oxide or propylene oxide; and can be converted by reaction with carboxylic acid chlorides or carboxylic acid anhydrides into the corresponding N-acyloxyalkyl groups. If $R^1$ is —O·, then such N-oxyls can be produced from the NH compounds by oxidation with peroxy acids or hydrogen peroxide. By reduction of such N-oxyls, for example by means of catalytic hydrogenation, there can be produced the compounds wherein $R^1$ denotes OH.

As the next step, there can be introduced into the compounds of the formula VI either firstly the substituent $R^2$ and subsequently $R^3$ or, preferably, firstly the substituent $R^3$ and then $R^2$.

The introduction of the hydroxybenzyl group $R^2$ can be effected by reaction with a hydroxybenzyldithiocarbamate of the formula $R^2$—S—CS—N($R^{21}$)$_2$, wherein $R^{21}$ represents an alkyl group having 1–5 carbon atoms, or both groups $R^{21}$ together with the nitrogen atom represent a morpholine, pyrrolidine or piperidine ring. Such dithiocarbamates are obtainable by reaction of a phenol with formaldehyde, carbon disulphide and a secondary amine.

The reaction of the dithiocarbamates with the compounds of the formula VI is performed in the molar ratio of 1:1 in the presence of basic reagents such as alkali hydroxides, alkali alcoholates, alkali hydrides or alkaline-earth hydrides or alkali amides. These bases are preferably used in molar amounts, i.e. there is added per mole of dithiocarbamate one equivalent of the base. The reaction can be performed in solution, for example in alcohols, ethers or hydrocarbons. Also suitable are polar aprotic solvents such as dimethylformamide or dimethylsulphoxide. The reaction is carried out preferably in an alcoholic solution with the use of alkali hydroxide as the base.

Another suitable method for introducing the hydroxybenzyl group $R^2$ into the comounds VI comprises reacting them with hydroxybenzylamines $R^2$—N($R^{21}$)$_2$. Such amines are obtainable by reaction of phenols with formaldehyde and a secondary amine in a so-called Mannich reaction. Their reaction with the compounds VI is likewise accelerated with basic catalysts, preferably with alkali amides or alkali alcoholates. Also alkali metals are suitable as catalysts. This process differs from the dithiocarbamate process, however, in that catalytic amounts, about 0.1 to 5 Mol-%, of basic catalyst are sufficient.

Instead of the tertiary amines (Mannich bases), there can also be used the quaternisation products thereof. The solvents employed can be those of the aforementioned classes: the reaction can however be performed also without solvent.

If X is oxygen, the radical $R^2$ can be introduced also in the manner of a malonic ester synthesis by firstly converting the ester VI by reaction with one equivalent of alkali metal, alkali alcoholate, alkali amide or alkali hydride, or of a similar basic alkali compound, into the alkali compound of VI, and subsequently reacting in the usual manner with 1 mole of a hydroxybenzyl halide $R^2$Hal (Hal=Cl, Br or J). Although the two aforementioned methods of hydroxybenzylation are preferred, the last-mentioned method can be of value in cases in which the halogen compound $R^2$Hal is readily available.

Each of the three described methods produces a hydroxybenzyl malonic acid derivative of the formula VII, into which the substituent $R^3$ has to be subsequently introduced:

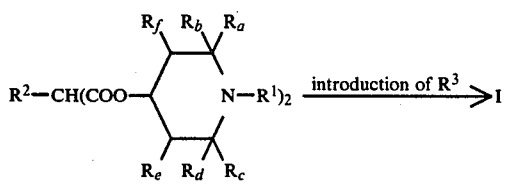

VII.

The introduction of the substituent $R^3$ can be effected by the conventional method of C-alkylation of malonic esters, whereby firstly VII is converted into its alkali compound, and this is then reacted with a halogen compound $R^3Hal$ or $R^3Hal_2$. Hal in this case again denotes Cl, Br or J. Depending on whether n is to be 1 or 2 in the compound of the formula I resulting from the synthesis, there is used per mole of alkali compound of VII one mole of a monohalide $R^3Hal$ or a half mole of a dihalogen compound $R^3Hal_2$. Examples of these are halides of alkyl, cycloalkyl, aralkyl, alkenyl or alkynyl, and dihalides of alkylene, alkenylene, alkynylene or xylylene. Further examples are halogenocarboxylic acid esters such as chloroacetic acid esters of mono- or bivalent hydroxyl compounds, or carboxylic acid esters of halogenohydrines such as esters of 2-chloroethanol or 3-bromopropanol. Also halogenophosphonic acid esters, such as dimethyl-chloromethylphosphonate or diethyl-2-bromoethylphosphonate, are suitable for this purpose.

If iodine is used instead of an organic halogen compound, there are obtained compounds of the formula I wherein n is 2 and $R^3$ is a direct bond.

In addition to this conventional method of C-substitution with halogen compounds, it is possible to use for the introduction of the radical $R^3$ the method of the so-called Michael addition, by which method compounds having activated double bonds can be added, under the influence of basic catalysts, to the central carbon atom of the compound VII. The best known sort of such reactions is the cyanoalkylation with acrylonitrile. Also suitable however are acrylic acid esters and methacrylic acid esters, maleic acid esters, itaconic acid esters, vinyl ketones, vinyl sulphones, vinyl esters of carboxylic acids or esters of vinylphosphonic acid. The catalysts employed for the purpose are used in amounts of about 0.5 to 5 Mol-%. Examples of applicable catalysts are again alkali alcoholates, alkali amides, alkali hydrides or alkali hydroxides, or quaternary ammonium bases such as benzyltrimethylammonium hydroxide. The reactions are preferably performed in solution both in the case of the conventional malonic acid substitution and in the case of the process of Michael addition. There can be used aprotic solvents such as hydrocarbons or ethers, for instance benzene, toluene, dioxane or tetrahydrofuran, or polar solvents such as dimethylformamide.

Compounds of the formula I wherein $R^3$ is a radical of the formula IV can be produced by condensation of two different malonic acid derivatives with formaldehyde in the approximate molar ratio 1:1:1, and subsequent introduction of one or two hydroxybenzyl groups.

Compounds of the formula I wherein $R^3$ is a group of the formula III can be obtained by condensation of a malonic acid derivative of the formula VI with a 4-oxopiperidine and subsequent hydrogenation of the formed piperidylidene compound.

A special method for the introduction of phosphonomethyl groups as substituent $R^3$ consists of reacting a malonic acid derivative VII with formaldehyde and a phosphite of the formula $P(OR^{14})_3$.

Furthermore, a specific substituent $R^3$ can be firstly introduced by one of the processes mentioned, and then converted in an additional reaction step into another group $R^3$. For example, it is possible by the addition of ethyl acrylate to introduce the group $R^3=CH_2CH_2COOC_2H_5$, which is then converted in a second step by transesterification with ethylene glycol into the bivalent group $R^3=-CH_2CH_2COOCH_2C-$ $H_2OOCCH_2CH_2$. In a similar manner, an intermediate halogenoalkyl group can be converted into a phenoxyalkyl or a phosphonoalkyl group. Alkylthioalkyl groups can be converted by oxidation into the corresponding sulphoxides or sulphones. This kind of oxidation of the substituent $R^3$ can be performed simultaneously with the introduction of oxygen as $R^1$, for example by oxidation with percarboxylic acids. The introduction of $R^1$ can also be performed together with the introduction of $R^3$ if $R^1$ and $R^3$ are identical, e.g. as alkyl, alkenyl, propargyl or benzyl.

By virtue of these various possibilites for the carrying out of the individual reaction steps, namely introduction of the piperidinyl radical, introduction of the group $R^2$, introduction of the group $R^3$, and optionally introduction of $R^1$, the sequence of the individual steps selected will be that which appears most advantageous for the case in question.

In the Examples subsequently given, the introduction of $R^2$ is described principally as the final step. Any other step however can essentially be selected as the final step.

If in the compounds of the formula VI, the substituent $R^3$ is firstly introduced according to the above-described methods, there are obtained the intermediates of the formula VIII

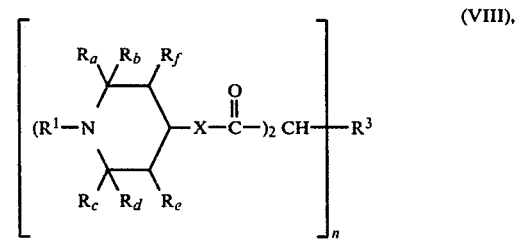

(VIII), which likewise are novel compounds.

The compounds of the formula I can be used according to the present invention as stabilisers for plastics to protect them from damage caused by the action of oxygen, heat and light. Examples of such plastics are the following polymers.

1. Polymers of monoolefines and diolefines, for example polyethylene (which optionally can be crosslinked), polypropylene, polyisobutylene, polymethylbutene-1, polymethylpentene-1, polyisoprene or polybutadiene.

2. Mixtures of the polymers mentioned under (1), for example mixtures of polypropylene with polyethylene or with polyisobutylene.

3. Copolymers of monoolefines and diolefines, such as, for example, ethylene/propylene copolymers, propylene/butene-1 copolymers, propylene/isobutylene copolymers, ethylene/butene-1 copolymers and also terpolymers of ethylene with propylene and a diene, such as hexadiene, dicyclopentadiene or ethylidenenorbornene.

4. Polystyrene.

5. Copolymers or styrene or α-methylstyrene, such as, for example, styrene/butadiene, styrene/acrylonitrile, styrene/acrylonitrile/methyl acrylate; mixtures, of high impact strength, of styrene copolymers and another polymer, such as, for example, a polyacrylate, a diene polymer or an ethylene/propylene/diene terpolymer; and block copolymers of styrene, such as, for example, styrene/butadiene/styrene, styrene/isoprene/styrene or styrene/ethylene/butylene/styrene.

6. Graft copolymers of styrene, such as, for example, styrene on polybutadiene, styrene and acrylonitrile on polybutadiene and mixtures thereof with the copolymers mentioned under (5), such as are known as so-called ABS polymers.

7. Halogen-containing polymers, such as, for example, polyvinyl chloride, polyvinylidene chloride, polyvinyl fluoride, polychloroprene, chlorinated rubbers and copolymers, such as vinyl chloride/vinylidene chloride, vinyl chloride/vinyl acetate or vinylidene chloride/vinyl acetate.

8. Polymers which are derived from $\alpha,\beta$-unsaturated acids and derivatives thereof, such as polyacrylates and polymethacrylates, polyacrylamides and polyacrylonitrile.

9. Polymers which are derived from unsaturated alcohols and amines or acyl derivatives or acetals thereof, such as polyvinyl alcohol, polyvinyl acetate, polyvinyl stearate, polyvinyl benzoate, polyvinyl maleate, polyvinylbutyral, polyallyl phthalate, polyallyl-melamine and copolymers thereof with other vinyl compounds, such as ethylene/vinyl acetate copolymers.

10. Homopolymers and copolymers of epoxides, such as polyethylene oxide, polypropylene oxide or polyisobutylene oxide.

11. Polyacetals, such as polyoxymethylene and those polyoxymethylenes which contain ethylene oxide as a comonomer.

12. Polyphenylene oxides.

13. Polyurethanes and polyureas.

14. Polycarbonates.

15. Polysulphones.

16. Polyamides and copolyamides which are derived from diamines and dicarboxylic acids and/or from aminocarboxylic acids or the corresponding lactams, such as polyamide 6, polyamide 6/6, polyamide 6/10, polyamide 11, polyamide 12 or poly-m-phenylene-isophthalamide.

17. Polyesters which are derived from dicarboxylic acids and dialcohols and/or from hydroxycarboxylic acids or the corresponding lactones, such as polyethylene terephthalate, polybutylene terephthlate and poly-1,4-dimethylol-cyclohexane terephthalate, as well as copolyether-esters, wherein all or a part of the used diol is an ether-diol or polyetherdiol.

18. Crosslinked polymers which are derived from aldehydes on the one hand and phenols, ureas and melamines on the other hand, such as phenol/formaldehyde resins, urea/formaldehyde resins and melamine/formaldehyde resins.

19. Alkyd resins, such as glycerol/phthalic acid resins and mixtures thereof with melamine/formaldehyde resins.

20. Unsaturated polyester resins which are derived from copolyesters of saturated and unsaturated dicarboxylic acids with polyhydric alcohols and vinyl compounds as crosslinking agents.

21. Crosslinked epoxide resins which are derived from polyepoxides, for example from bis-glycidyl ethers or from cycloaliphatic diepoxides.

22. Natural polymers, such as cellulose, rubber, proteins and derivatives thereof which are chemically modified in a polymer-homologous manner, such as cellulose acetates, cellulose propionates and cellulose butyrates, or cellulose ethers, such as methylcellulose.

Of particular importance is the stabilisation of polyolefins, styrene polymers and polyurethanes, for which the malonates of the formula I are excellently suitable. Examples of such plastics are: polyethylene of high and of low density, polypropylene, ethylene/propylene copolymers, polystyrene, styrene/butadiene/acrylonitrile copolymers, mixtures of polyolefins or of styrene polymers, polyurethanes based on polyether or polyester—in the form of lacquers, elastomers or foam plastics.

The stabilisers are added to the plastics at a concentration of 0.01 to 5 percent by weight, calculated on the material to be stabilised. There is preferably incorporated into the material 0.03 to 1.5 percent by weight, particularly preferably 0.2 to 0.6 percent by weight, of the compounds, relative to the material to be stabilised.

Incorporation can be effected after polymerisation, for example by the mixing of the compounds and, optionally, further additives into the melt, by methods normally used in industry, either before or during moulding; or by application of the dissolved or dispersed compounds to the polymers, optionally with subsequent removal of the solvent by evaporation.

The new compounds can be added also in the form of a master batch, which contains these compounds for example at a concentration of 2.5 to 25 percent by weight, to the plastics to be stabilised.

In the case of cross-linked polyethylene, the compounds are added before cross-linking.

In addition to the compounds of the formula I, there can be added to the plastics also known stabilisers or co-stabilisers. These can be, e.g., antioxidants, light stabilisers or metal-deactivators; or co-stabilisers such as those of the phosphorous acid ester type. There can also be added other additives common in plastics technology, such as flameproofing agents, antistatic agents, plasticisers, lubricants, blowing agents, pigments, reinforcing substances or fillers.

The invention therefore relates also to the plastics stabilised by the addition of 0.01 to 5 percent by weight of a compound of the formula I, which plastics can if required also contain known conventional additives. The plastics stabilised in this manner can be employed in the most varied forms, e.g. as sheet, fibres, tapes or profiles, or as binders for lacequers, adhesives or cements.

The invention relates further to the compounds of the formula VIII and to their use as light stabilisers for plastics. The substrates, quantity ratios and processes of incorporation suitable for this purpose are the same as those for the use of the compounds of the formula I.

The manufacture and the use of the compounds of the invention are further illustrated in the following Examples. The term 'parts' denotes parts by weight, and % denotes percent by weight. Temperature values are given in degrees Centigrade.

EXAMPLES 1–32

23.3 g (0.05 mole) of butylmalonic acid-bis-(1,2,2,6,6-pentamethyl-4-piperidinyl)-ester and 13.2 g (0.05 mole) of N-(3,5-di-tert.butyl-4-hydroxybenzyl)dimethylamine are dissolved in 200 ml of toluene. After the addition of 0.25 g of lithium amide, the mixture is refluxed for 4 hours. After cooling, the mixture is neutralised with 1.5 ml of 1% acetic acid, and the organic phase is repeatedly washed with water. After drying over $Na_2SO_4$, the solution is concentrated in vacuo. There is obtained butyl-(3,5-di-tert.butyl-4-hydroxybenzyl)-malonic acid-bis (1,2,2,6,6-pentamethyl-4-piperidinyl)-ester having a melting point of 140° C.

The compounds described in Table I are produced in an analogous manner.

Table I $$\left[ (R^1-N)\begin{array}{c}CH_3\ CH_3\\ \\ CH_3\ CH_3\end{array} O-\overset{O}{\underset{\|}{C}}{-})_2\overset{R^2}{\underset{}{C}}-R^3 \right]_n$$

| Comp. No. | n | R¹ | R² | R³ | Name | Physical properties |
|---|---|---|---|---|---|---|
| 2 | 1 | H | t-C₄H₉, HO–⌬–CH₂–, t-C₄H₉ | —C₄H₉ | butyl-(3,5-di-tert. butyl-4-hydroxy-benzyl)-malonic acid-bis(2,2,6,6-tetramethyl-4-piperidinyl)ester | m.p. 125° C. |
| 3 | 1 | H | t-C₄H₉, HO–⌬–CH₂–, CH₃ | —C₄H₉ | butyl-(3-methyl-5-tert.butyl-4-hydroxy-benzyl)-malonic acid-bis(2,2,6,6-tetramethyl-4-piperidinyl)ester | m.p. 157° C. |
| 4 | 1 | CH₃ | t-C₄H₉, HO–⌬–CH₂–, CH₃ | —C₄H₉ | butyl-(3-methyl-5-tert.butyl-4-hydroxy-benzyl)-malonic acid-bis(1,2,2,6,6-pentamethylpiperidinyl)ester | m.p. 150° C. |
| 5 | 1 | O | t-C₄H₉, HO–⌬–CH₂–, t-C₄H₉ | —C₄H₉ | butyl-(3,5-di-tert. butyl-4-hydroxy-benzyl)-malonic acid-bis(1-oxyl-2,2,6,6-tetramethyl-4-piperidinyl)ester | m.p. 145° C. |
| 6 | 1 | CH₃CO | t-C₄H₉, HO–⌬–CH₂–, t-C₄H₉ | —C₄H₉ | butyl-(3,5-di-tert. butyl-4-hydroxy-benzyl)-malonic acid-bis(1-acetyl-2,2,6,6-tetramethyl-4-piperidinyl)ester | m.p. 136° C. |
| 7 | 1 | H | t-C₄H₉, HO–⌬–CH₂–, CH₃ | —CH(CH₃)₂ | isopropyl-(3-methyl-5-tert.butyl-4-hydroxybenzyl)-malonic acid-bis(2,2,6,6-tetramethyl-4-piperidinyl)ester | oil |
| 8 | 1 | CH₃ | t-C₄H₉, HO–⌬–CH₂–, CH₃ | —CH₃ | methyl-(3-methyl-5-tert.butyl-4-hydroxy-benzyl)-malonic acid-bis(1,2,2,6,6-pentamethyl-4-piperidinyl)ester | m.p. 137° C. |
| 9 | 1 | CH₃ | t-C₄H₉, HO–⌬–CH₂–, t-C₄H₉ | —CH₂—P(OC₂H₅)₂ (with =O) | diethylphosphonomethyl-(3,5-di-tert. butyl-4-hydroxy-benzyl)-malonic acid-bis(1,2,2,6,6-pentamethyl-4-piperidinyl)ester | viscous oil |
| 10 | 1 | H | t-C₄H₉, HO–⌬–CH₂–, CH₃ | —CH₂CH=CH₂ | allyl-(3-methyl-5-tert.butyl-4-hydroxy-benzyl)-malonic acid-bis(2,2,6,6-tetramethyl-4-piperidinyl)ester | m.p. 150° C. |
| 11 | 1 | H | t-C₄H₉, HO–⌬–CH₂–, t-C₄H₉ | —(CH₂)₃—P(O)(OC₂H₅)₂ | 3'-diethylphosphonopropyl-(3,5-di-tert. butyl-4-hydroxy-benzyl)-malonic acid-bis(2,2,6,6-tetramethyl-4-piperidinyl)ester | m.p. 134° C. |

Table I-continued $$\left[(R^1-N\underset{CH_3\ CH_3}{\overset{CH_3\ CH_3}{\diagup}}O-\overset{O}{\overset{\|}{C}}-\right)_2 \overset{R^2}{\underset{}{C}}-R^3\right]_n$$

| Comp. No. | n | R¹ | R² | R³ | Name | Physical properties |
|---|---|---|---|---|---|---|
| 12 | 1 | H | t-C₄H₉, HO-⌬-CH₂- (with t-C₄H₉) | —C₈H₁₇(n) | octyl-(3,5-di-tert.butyl-4-hydroxybenzyl)-malonic acid-bis(2,2,6,6-tetramethyl-piperidinyl) ester | oil |
| 13 | 1 | CH₃ | t-C₄H₉, HO-⌬-CH₂- (with t-C₄H₉) | —C₁₂H₂₅(n) | dodecyl-(3,5-di-tert.butyl-4-hydroxybenzyl)-malonic acid-bis(1,2,2,6,6-pentamethyl-4-piperidinyl) ester | m.p. 126° C. |
| 14 | 1 | CH₃ | t-C₄H₉, HO-⌬-CH₂- (with CH₃) | —CH₂—C(=O)—O—(1,2,2,6,6-pentamethyl-4-piperidinyl) | 1,2,2,6,6-pentamethyl-4-piperidinyl-oxycarbonylmethyl-(3-methyl-5-tert.butyl-4-hydroxybenzyl)-malonic acid-bis(1,2,2,6,6-pentamethyl-4-piperidinyl) ester | m.p. 150° C. |
| 15 | 1 | CH₃ | t-C₄H₉, HO-⌬-CH₂- (with t-C₄H₉) | —CH₂—C(=O)—O—(1,2,2,6,6-pentamethyl-4-piperidinyl) | 1,2,2,6,6-pentamethyl-4-piperidinyl-oxycarbonylmethyl (3,5-di-tert.butyl-4-hydroxybenzyl)-malonic acid-bis(1,2,2,6,6-pentamethyl-4-piperidinyl)ester | m.p. 160° C. |
| 16 | 1 | H | t-C₄H₉, HO-⌬-CH₂- (with CH₃) | —C₁₈H₃₇(n) | octadecyl-(3-methyl-5-tert.butyl-4-hydroxybenzyl) malonic acid-bis(2,2,6,6-tetramethyl-4-piperidinyl)ester | oil |
| 17 | 1 | H | t-C₄H₉, HO-⌬-CH₂- (with CH₃) | —CH₂—C(=O)—O—(2,2,6,6-tetramethyl-4-piperidinyl, NH) | 2,2,6,6-tetramethyl-4-piperidinyloxy-carbonylmethyl-(3-methyl-5-tert.butyl-4-hydroxybenzyl)-malonic acid-bis(2,2,6,6-tetramethyl-4-piperidinyl)ester | m.p. 104° C. |
| 18 | 1 | H | t-C₄H₉, HO-⌬-CH₂- (with t-C₄H₉) | —CH₂—C(=O)—O—(2,2,6,6-tetramethyl-4-piperidinyl, NH) | 2,2,6,6-tetramethyl-4-piperidinyloxy-carbonylmethyl-(3,5-di-tert.butyl-4-hydroxybenzyl)-malonic acid-bis-(2,2,6,6-tetramethyl-4-piperidinyl)ester | m.p. 170° C. |
| 19 | 2 | CH₃ | t-C₄H₉, HO-⌬-CH₂- (with t-C₄H₉) | — | 1,4-di(3,5-di-tert.butyl-4-hydroxyphenyl)-2,2,3,3-tetra-(1,2,2,6,6-pentamethyl-4-piperidinyloxy-carbonyl)butane | viscous oil |
| 20 | 2 | H | t-C₄H₉, HO-⌬-CH₂- (with CH₃) | —(CH₂)₃— | 1,7-di(3-methyl-5-tert.butyl-4-hydroxyphenyl)-2,2,6,6-tetra(2,2,6,6-tetramethyl-4-piperidinyloxycarbonyl)-heptane | oil |

Table I-continued

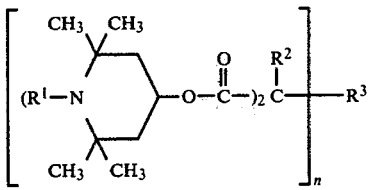

| Comp. No. | n | R¹ | R² | R³ | Name | Physical properties |
|---|---|---|---|---|---|---|
| 21 | 1 | CH₃ | t-C₄H₉, HO-⌬-CH₂, t-C₄H₉ | —CH(CH₃)₂ | isopropyl-(3,5-di-tert.butyl-4-hydroxy-benzyl)-malonic acid-bis-(1,2,2,6,6-tetramethyl-4-piperidinyl) ester | m.p. 125° C. |
| 22 | 1 | CH₃ | t-C₄H₉, HO-⌬-CH₂—, t-C₄H₉ | —CH₂CH₂COOCH₃ | methoxycarbonylethyl-(3,5-di-tert.butyl-4-hydroxybenzyl)-malonic acid-bis-(1,2,2,6,6-tetramethyl-4-piperidinyl)ester | m.p. 165° C. |
| 23 | 1 | CH₃ | t-C₄H₉, HO-⌬-CH₂—, t-C₄H₉ | —C₆H₅ (phenyl) | phenyl-(3,5-di-tert.butyl-4-hydroxy-benzyl)-malonic acid-bis-(1,2,2,6,6-tetra-methyl-4-piperidinyl)ester | oil |
| 24 | 1 | CH₃ | t-C₄H₉, HO-⌬-CH₂—, t-C₄H₉ | —CH₂—C₆H₅ | benzyl-(3,5-di-tert. butyl-4-hydroxy-benzyl)-malonic-acid-bis-(1,2,2,6,6-tetramethyl-4-piperidinyl)ester | m.p. 152° C. |
| 25 | 1 | CH₃ | t-C₄H₉, HO-⌬-CH₂—, t-C₄H₉ | —CH₂—CH(CH₃)—C(O)—O—(2,2,6,6-tetramethyl-4-piperidinyl) | 2-(2,2,6,6-tetra-methyl-4-piperi-dinyloxycarbonyl)-propyl-malonic acid-bis-(1,2,2,6,6-tetramethyl-4-piperi-dinyl)ester | m.p. 143° C. |
| 26 | 1 | n-C₃H₇ | t-C₄H₉, HO-⌬-CH₂—, t-C₄H₉ | —C₄H₉ | butyl-(3,5-di-tert. butyl-4-hydroxy-benzyl)-malonic acid-bis-(1-propyl-2,2,6,6-tetramethyl-4-piperidinyl)ester | m.p. 142° C. |
| 27 | 1 | CH₂=CH—CH₂— | t-C₄H₉, HO-⌬-CH₂—, t-C₄H₉ | —C₄H₉ | butyl-(3,5-di-tert. butyl-4-hydroxy-benzyl)-malonic acid-bis-(1-allyl-2,2,6,6-tetra-methyl-4-piperi-dinyl)ester | m.p. 148° C. |
| 28 | 1 | CH₃ | t-C₄H₉, HO-⌬-CH₂—, t-C₄H₉ | —NHCOCH₃ | acetamino-(3,5-di-tert. butyl-4-hydroxybenzyl)-malonic acid-bis-(1,2,2,6,6-penta-methyl-4-piperi-dinyl)ester | m.p. 225° C. |
| 29 | 2 | H | t-C₄H₉, HO-⌬-CH₂—, t-C₄H₉ | —(CH₂)₁₂— | 1,16-di-(3,5-di-tert. butyl-4-hydroxyphenyl)-2,2,15,15-tetra-(2,2,6,6-tetramethyl-4-piperidinyloxy-carbonyl)-hexadecane | m.p. 130°-6° C. |
| 30 | 1 | CH₃ | t-C₄H₉, HO-⌬-CH₂—, t-C₄H₉ | —O—C(O)—(3,5-di-t-C₄H₉-4-OH-phenyl) | 3,5-di-tert. butyl-4-hydroxybenzoyloxy-(3,5-di-tert. butyl-4-hydroxybenzyl)-malonic acid-bis-(1,2,2,6,6-pentamethyl-4-piperidinyl)ester | m.p. 213°-4° C. |

Table I-continued

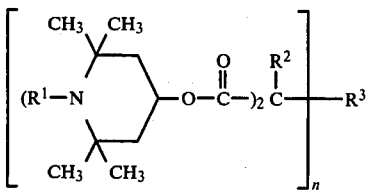

| Comp. No. | n | R¹ | R² | R³ | Name | Physical properties |
|---|---|---|---|---|---|---|
| 31 | 1 | $CH_3$ | t-$C_4H_9$, HO–⌬–$CH_2$– , t-$C_4H_9$ | –CH(COO–piperidinyl)–$CH_2$–COO–piperidinyl (where piperidinyl = 1,2,2,6,6-pentamethyl-4-piperidinyl) | 3,4,4-tris-(1,2,2,6,6-pentamethyl-4-piperidinyloxy-carbonyl)-5-(3,5-di-tert. butyl-4-hydroxyphenyl)-valeric acid-(1,2,2,6,6-pentamethyl-4-piperidinyl)ester | oil |

EXAMPLES 32–35

26.2 g (0.05 mole) of butylmalonic acid-bis(2,3,6-trimethyl-2,6-diethyl-4-piperidinyl)ester and 13.2 g (0.05 mole) of N-(3,5-di-tert.butyl-4-hydroxybenzyl) dimethylamine are dissolved in 200 ml of toluene. After the addition of 0.25 g of lithium amide, the mixture is refluxed for 4 hours. After cooling, the mixture is neutralised with 1.5 ml of 1% acetic acid, and the organic phase is repeatedly washed with water. After drying over $Na_2SO_4$, the solution is concentrated in vacuo. As residue there is obtained butyl-(3,5-di-tert.butyl-4-hydroxybenzyl)malonic acid-bis(2,3,6-trimethyl-2,6-diethyl-4-piperidinyl) ester in the form of viscous oil (Compound No. 32).

Analysis: for $C_{46}H_{80}N_2O_5$. Calculated: C, 74.54%; H, 10.88%; N, 3.78%; Found: C, 74.7%; H, 10.6%; N, 3.82%.

The compounds described in Table Ia are produced in an analogous manner.

Table Ia

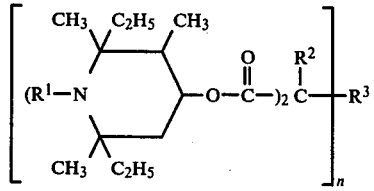

| Comp. No. | n | R¹ | R² | R³ | Name | Physical properties |
|---|---|---|---|---|---|---|
| 33 | 1 | H | t-$C_4H_9$, HO–⌬–$CH_2$, $CH_3$ | —$C_4H_9$ | butyl-(3-methyl-5-tert.butyl-4-hydroxy-benzyl)-malonic acid-bis-(2,3,6-trimethyl-2,6-diethyl-4-piperidinyl)ester | oil |
| 34 | 1 | H | t-$C_4H_9$, HO–⌬–$CH_2$–, $CH_3$ | —$C_8H_{17}$ | octyl-(3-methyl-5-tert.butyl-4-hydroxy-benzyl)-malonic acid-bis-(2,3,6-trimethyl-2,6-diethyl-4-piperidinyl)ester | oil |
| 35 | 1 | H | t-$C_4H_9$, HO–⌬–$CH_2$–, t-$C_4H_9$ | —$C_{12}H_{25}$ | docecyl-(3,5-di-tert. butyl-4-hydroxy-benzyl)-malonic acid-bis-(2,3,6-trimethyl-2,6-diethyl-4-piperidinyl)ester | oil |

EXAMPLES 36–42

13.2 g (0.03 mole) of ethylmalonic acid-bis(1,2,2,6,6-pentamethyl)-ester and 9.75 g (0.03 mole) of N-diethyl-S-(3,5-di-tert.butyl-4-hydroxybenzyl)dithiocarbaminate are dissolved in 100 ml of isopropanol. There is then added dropwise with stirring, in the course of 15 minutes at 60°, 1.2 g of NaOH (0.03 mole) in 12 ml of water. The mixture is subsequently refluxed for 2 hours and afterwards cooled to 50°; an addition is made of 36 ml of 1% acetic acid, and the whole is cooled to 0°, whereupon the product crystallises and is subsequently recrystallised from ligroin to obtain 12.7 g of ethyl(3,5-di-tert.butyl-4-hydroxybenzyl)-malonic acid-bis(1,2,2,6,6-pentamethyl-4-hydroxybenzyl)-ester, m.p. 166° C.

The compounds listed in Tables IIa and IIb are produced analogously with the use of the corresponding dithiocarbamates:

No. 44: ethyl-(2,6-dimethyl-4-tert.butyl-3-hydroxybenzyl)-malonic acid-bis(1,2,2,6,6-pentamethyl-4-piperidinyl) ester, m.p. 175° C.;

No. 45: butyl-(2,6-dimethyl-4-tert.butyl-3-hydroxybenzyl)-malonic acid-bis(1,2,2,6,6-pentamethyl-4-piperidinyl) ester; yellow oil;

No. 46: butyl-(2,6-dimethyl-4-tert.butyl-3-hydroxybenzyl) malonic acid-bis(2,2,6,6-tetramethyl-4-piperidinyl) ester; oil.

EXAMPLE 47

21.9 g (0.05 mole) of ethylmalonic acid-bis-(1,2,2,6,6-

Table IIa

| Comp. No. | $R^1$ | $R^7$ | $R^8$ | $R^3$ | Name | Physical properties |
|---|---|---|---|---|---|---|
| 37 | H | $CH_3$ | H | $-C_2H_5$ | ethyl-(3-methyl-5-tert.butyl-4-hydroxybenzyl)-malonic acid-bis(2,2,6,6-tetramethyl-4-piperidinyl)ester | m.p. 104° C. |
| 38 | H | $t-C_4H_9$ | H | $-C_2H_5$ | ethyl-(3,5-di-tert.butyl-4-hydroxybenzyl)-malonic acid-bis(2,2,6,6-tetramethyl-4-piperidinyl)ester | m.p. 144° C. |
| 39 | $CH_3$ | $CH_3$ | H | $-C_2H_5$ | ethyl-(3-methyl-5-tert.butyl-4-hydroxybenzyl)-malonic acid-bis(1,2,2,6,6-pentamethyl-4-piperidinyl)ester | m.p. 153° C. |
| 40 | H | $CH_3$ | $CH_3$ | $-C_8H_{17}$ | octyl-(2,3-dimethyl-5-tert.butyl-4-hydroxybenzyl)-malonic acid-bis(2,2,6,6-tetramethyl-4-piperidinyl)ester | viscous oil |

Table IIb

| Comp. No. | n | $R^1$ | $R^7$ | $R^3$ | Name | Physical properties |
|---|---|---|---|---|---|---|
| 41 | 1 | $CH_3$ | $t-C_4H_9$ | phenyl | phenyl-(3,5-di-tert. butyl-4-hydroxybenzyl)-malonic acid-bis-(1,2,3,6-tetramethyl-2,6-diethyl-4-piperidinyl)ester | oil |
| 42 | 2 | H | $CH_3$ | $-(CH_2)_6-$ | 1,10-di-(3-methyl-4-hydroxy-5-tert. butylphenyl)-2,2,9,9-tetra-(2,3,6-trimethyl-2,6-diethyl-4-4-piperidinyloxycarbonyl)decane | oil |

EXAMPLES 43–46

To 24.6 g (0.06 mole) of ethylmalonic acid-bis(2,2,6,6-tetramethyl-4-piperidinyl)ester in 80 ml of dimethylformamide there are added 2.5 g of NaH dispersion (55–60%) followed by 13.6 g (0.06 mole) of 2,6-di-methyl-4-tert. butyl-3-hydroxybenzyl chloride in 40 ml of DMF. The reaction mixture is stirred for 20 hours at 90°–100° C. and is then poured into ice-water; the aqueous solution is extracted with ether, the ethereal solution is dried over $Na_2SO_4$, and after removal of the solvent in vacuo there is obtained ethyl-(2,6-dimethyl-4-tert.butyl-3-hydroxybenzyl)malonic acid-bis (2,2,6,6-tetramethyl-4-piperidinyl)ester in the form of an oily yellowish residue (No. 43).

The following are produced in an analogous manner:

pentamethyl-4-piperidinyl)ester, 20.5 g (0.05 mole) of malonic acid-bis-(1,2,2,6,6-pentamethyl-4-piperidinyl)ester, 1.5 g (0.05 mole) of paraformaldehyde and 0.5 g of NaH are stirred in 120 ml of toluene for half an hour at room temperature and then for 7 hours at reflux temperature. After cooling, there is added 13.2 g (0.05 mole) of N-(3,5-di-tert.butyl-4-hydroxybenzyl)-dimethylamine, and the mixture is heated for 4 hours under reflux. Processing analogously to Example 1 yields 1-(3,5-di-tert.butyl-4-hydroxyphenyl)-2,2,4,4-tetra-(1,2,2,6,6-pentamethyl-4-piperidinyloxycarbonyl)-hexane as an oily residue.

Analysis: Calculated: C, 71.2%; H, 10.3%; N, 5.2%; Found: C, 70.3%; H, 10.5%; N, 5.3%.

EXAMPLES 48 AND 49

39 g of butyl-(3,5-di-tert.butyl-4-hydroxybenzyl)-malonic acid-bis(2,3,6-trimethyl-2,6-diethyl-4-piperidinyl)ester (Compound No. 32) is dissolved in 200 ml of xylene. 20 g of anhydrous potassium carbonate and 10 g of acetic acid anhydride are added at room temperature, and the suspension is slowly heated until an intense generation of $CO_2$ commences. As soon as the generation of $CO_2$ subsides, the temperature is further raised to 130°–135° C. and stirring is maintained for 10 hours with refluxing. After cooling, the potassium salts are filtered off and the xylene solution is concentrated in vacuo. There remains a brownish viscous oil which is crude butyl-(3,5-di-tert.butyl-4-hydroxybenzyl)-malonic acid-bis (1-acetyl-2,3,6-trimethyl-2,6-diethyl-4-piperidinyl)ester.

Analysis: Calculated: C, 72.77%; H, 10.26%; N, 3.39%; Found: C, 72.8%; H, 10.1%; N, 3.50%.

In an analogous manner, 32 g of butyl-(3,5-di-tert.butyl-4-hydroxybenzyl)-malonic acid-bis-(2,2,6,6-tetramethyl-4-piperidinyl)ester is reacted with 10 g of acetic acid anhydride and 20 g of $K_2CO_3$. There is obtained butyl-(3,5-di-tert.butyl-4-hydroxybenzyl)-malonic acid-bis-(1-acetyl-2,2,6,6-tetramethyl-4-piperidinyl)ester, which melts at 120°–124° C.

EXAMPLE 50

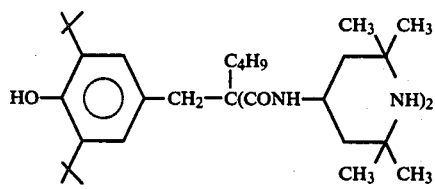

43 g of butylmalonic acid-N,N'-di-(2,2,6,6-tetramethyl-4-piperidinyl)-diamide (0.1 mole) and 26.4 g of N-(3,5-di-tert.butyl-4-hydroxybenzyl)-dimethylamine (0.1 mole) are refluxed in 450 ml of toluene with the addition of 0.5 g of $LiNH_2$ for 4 hours. After cooling, the reaction mixture is neutralised with 0.4 g of glacial acetic acid, filtered and concentrated by evaporation. As residue is obtained crude butyl-(3,5-di-tert.butyl-4-hydroxybenzyl)-malonic acid-N,N'-di-(2,2,6,6-tetramethyl-4-piperidinyl)-diamide, which melts at 244° C. after recrystallisation from ethanol.

EXAMPLE 51

100 parts of polypropylene (melt index 3.2 g/10 min., 230°/2160 g) are thoroughly mixed for 10 minutes, in a shaking apparatus, with 0.2 part of one of the stabilisers given in the following Table. The mixture obtained is kneaded in a Brabender plastograph at 200° for 10 minutes; the material produced in this manner is then pressed in a platen press at 260° platen temperature to form 1 mm thick sheets, from which are stamped strips 1 cm wide and 17 cm long.

The test for effectiveness of the additives contained in the test strips is carried out by heat ageing in an air-circulation furnace at 135° and 149°, with an additive-free test strip serving as a comparison. Three test strips are used for each formulation. The end point of the test is defined as being the point at which an easily visible crumbling of the test strip commences.

Table III

| Stabiliser Example No. | Days until decomposition commences | |
|---|---|---|
| | 149° | 135° |
| none | 1 | 3 |
| 1 | 27 | 84 |
| 2 | 9 | 55 |
| 3 | 20 | 51 |
| 4 | 25 | 66 |
| 6 | 21 | 68 |
| 8 | 23 | 65 |
| 11 | 26 | 77 |
| 13 | 49 | 141 |
| 15 | 45 | 103 |
| 16 | 29 | 96 |
| 29 | 20 | 20 |
| 32 | 27 | 81 |
| 36 | 25 | 66 |
| 37 | 8 | 45 |
| 38 | 8 | 43 |
| 42 | 16 | 16 |
| 45 | 28 | 77 |
| 48 | 14 | 53 |

EXAMPLE 52

Some of the test specimens described in Example 51 are additionally tested for their colour stability, the test being made:

(a) after incorporation (Tab. IV, Col. 2);

(b) after 500 hours of irradiation in a Xenotest apparatus [Hanau] (Tab. IV, Col. 3);

(c) after 1-week's treatment with boiling water (Tab. IV, Col. 4).

For an assessment of the degree of discolouration there is used an empirical scale of values in which 5 denotes colourlessness, 4 a slight discolouration that is just perceptible, and 3, 2 and 1 denote successively higher degrees of discolouration.

Table IV

| Stabiliser Example No. | Assessment of discolouration on the basis of the Scale 1–5 | | |
|---|---|---|---|
| | After incorporation | After irradiation | Boiling water for 1 week |
| 1 | 4–5 | 5 | 4–5 |
| 2 | 4–5 | 5 | 5 |
| 3 | 4–5 | 5 | 4–5 |
| 4 | 4–5 | 5 | 4–5 |
| 36 | 4–5 | 5 | 4–5 |
| 37 | 4–5 | 5 | 4–5 |
| 38 | 4–5 | 5 | 4 |

EXAMPLE 53

100 parts of polypropylene powder (Moplen, fibre grade, Montedison) are homogenised with 0.2 part of β-(3,5-di-tert.butyl-4-hydroxyphenyl)propionic acid-octadecyl ester and 0.25 part of a stabiliser from the following Table V at 200° in a Brabender plastograph for 10 minutes. The mixture thus obtained is removed as quickly as possible from the kneading machine, and is then pressed out in a toggle press to give 2 to 3 mm thick sheet. A portion of the pressed sheet obtained is cut out and subsequently pressed between two highly polished hard-aluminium sheets in a hand-hydraulic laboratory press for 6 minutes at 260° under a pressure of 12 tons to form a sheet having a thickness of 0.5 mm, which is immediately quenched in cold water. From this 0.5 mm thick sheet there are prepared under exactly identical conditions the 0.1 mm thick test sheet. Test specimens each 60×44 mm in size are then stamped out from this sheet, and are irradiated in a Xenotest 150. At regular intervals of time, these specimens are removed from the irradiation apparatus and tested in an IR-spectrophotmeter for their carbonyl content. The increase of the carbonyl extinction at 5.85μ on irradiation is a measure for the photooxidative degradation of the polymer (see L. Balaban et al., J. Polymer Sci. Part C, 22, 1059-1071 (1969); J. F. Heacock, J. Polymer Sci. Part A-1, 22, 2921-34 (1969); D. J. Carlsson and D. M. Wiles, Macromolecules 2, 587-606 (1969)), and is from experience associated with a decrease of the mechanical properties of the polymer. Thus, for example, the sheet is completely brittle with the attainment of a carbonyl extinction of about 0.300.

The protective action of the stabilisers of the invention can be clearly seen from the following Table V:

Table V

| Stabiliser Example No. | Irradiation time in hours until CO-extinction = 0.3 |
|---|---|
| comparison | 800 |
| 1 | >5000 |
| 2 | 7700 |
| 3 | >5000 |
| 4 | >5000 |
| 32 | >5000 |
| 36 | >5000 |
| 37 | >5000 |
| 38 | >5000 |
| 42 | >5000 |
| 48 | >5000 |

I claim:
1. A member selected from the group consisting of a compound of the formula (I)

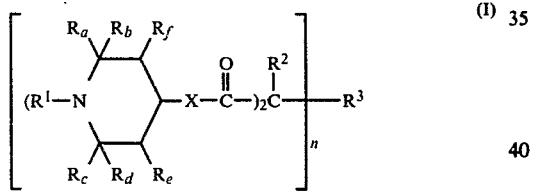

and an acid addition salt thereof, wherein
n is 1 or 2,
$R_a$ represents alkyl having 1-6 carbon atoms,
$R_b$ represents alkyl having 1-6 carbon atoms,
$R_c$ represents alkyl having 1-9 carbon atoms, phenyl, benzyl or phenylethyl,
$R_d$ represents alkyl having 1-6 carbon atoms, or
$R_c$ and $R_d$ together represent tetra- or pentamethylene,
$R_e$ represents hydrogen, alkyl having 1-5 carbon atoms, alkenyl having 3-4 carbon atoms, alkynyl having 3-4 carbon atoms or aralkyl having 7-8 carbon atoms,
$R_f$ represents hydrogen, alkyl having 1-5 carbon atoms, alkenyl having 3-4 carbon atoms, alkynyl having 3-4 carbon atoms, or aralkyl having 7-8 carbon atoms, with $R_e$ and $R_f$ being mutually exchangeable, and
X represents oxygen or —NR—,
R represents hydrogen, alkyl having 1-18 carbon atoms, alkenyl having 3-4 carbon atoms, alkynyl having 3-4 carbon atoms, cycloalkyl having 5-12 carbon atoms, aryl having 6-10 carbon atoms, or aralkyl having 7-9 carbon atoms,
$R^1$ represents hydrogen, —O·, —OH, alkyl having 1-12 carbon atoms, alkenyl having 3 or 4 carbon atoms, propargyl, benzyl or a group of the formula —CH$_2$—CH(OR$^5$)—R$^4$ wherein R$^4$ represents hydrogen, methyl or phenyl, and R$^5$ represents hydrogen or a group A—CO—, or R$^1$ represents a group A—CO—, and in both cases A represents alkyl having 1-12 carbon atoms, alkenyl having 2 or 3 carbon atoms, cyclohexyl, phenyl, benzyl, a phenyl or phenylethyl group substituted by 2 alkyl groups each having 1-4 carbon atoms and a hydroxyl group, alkylamino having 1-12 carbon atoms, dialkylamino having 2-16 carbon atoms, anilino, alkoxy having 1-12 carbon atoms, benzyloxy or phenoxy,
$R^2$ represents a hydroxybenzyl group of the formula II

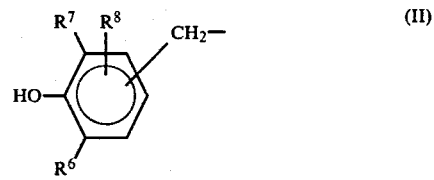

wherein $R^6$ and $R^7$ each independently represent an alkyl group having 1-9 carbon atoms, aralkyl having 7-9 carbon atoms or cycloalkyl having 5-8 carbon atoms, and $R^8$ represents hydrogen or methyl, and
$R^3$ represents, in the case where n is 1, alkyl having 1-20 carbon atoms, or alkyl having 1-10 carbon atoms, which is substituted by at least one of the groups —OR$^9$, —SR$^{10}$, —CO-R$^{11}$, —CN, —C(O)—YR$^{12}$, —O—C(O)R$^{13}$ or —P(O)(OR$^{14}$)$_2$, wherein
$R^9$ denotes phenyl or alkylphenyl having 7-10 carbon atoms, benzyl or cyclohexyl,
$R^{10}$ represents phenyl or alkylphenyl having 7-10 carbon atoms,
$R^{11}$ denotes alkyl having 1-12 carbon atoms,
Y denotes oxygen or —NR—, and R has the above-given meaning,
$R^{12}$ denotes alkyl having 1-18 carbon atoms, cycloalkyl having 5-12 carbon atoms, or a group of the formula III

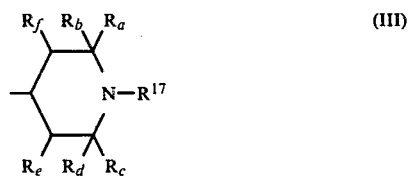

wherein $R^{17}$ has one of the meanings given for $R^1$
$R^{13}$ denotes alkyl having 1-17 carbon atoms, cycloalkyl having 5-12 carbon atoms, or phenyl or phenylalkyl having 7-9 carbon atoms, wherein the phenyl radical is unsubstituted or substituted by at least one of the groups alkyl having 1-4 carbon atoms and hydroxyl, and
$R^{14}$ denotes alkyl having 1-8 carbon atoms, allyl or phenyl, and X has the above-defined meaning, and
$R^3$ further represents an alkyl group having 2-22 carbon atoms, which is interrupted by —O—, —S—, —SO— or —SO$_2$—, alkenyl having 3-18 carbon atoms, alkynyl having 3-8 carbon atoms, cycloalkyl having 5-12 carbon atoms, alkylcycloalkyl having 6-18 carbon atoms, cycloalkylalkyl having 6-14 carbon atoms, aralkyl or alkylaralkyl having 7-19 carbon atoms, phenyl, or a group —$OR^{15}$, wherein $R^{15}$ is alkyl having 1-18 carbon atoms, alkenyl having 3-4 carbon atoms, alkynyl having 3-4 carbon atoms, cycloalkyl having 5-12 carbon atoms or aralkyl having 7-9 carbon atoms, or $R^3$ represents a group —O—C(O)$R^{16}$ or —NH—C(O)$R^{16}$, wherein $R^{16}$ is alkyl having 1-12 carbon atoms, alkenyl having 2 or 3 carbon atoms, cyclohexyl, phenyl, benzyl, a phenyl or phenylethyl group substituted by 2 alkyl groups each having 1-4 carbon atoms and a hydroxyl group, or $R^3$ is a group of the formula III or of the formula IV

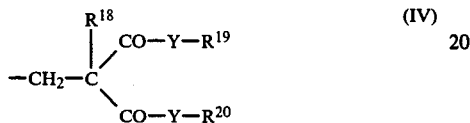

wherein $R^{18}$ represents alkyl having 1-20 carbon atoms, allyl, benzyl, phenyl, cyclohexyl, alkoxyalkyl- having 3-8 carbon atoms, or a group —O—C(O)$R^{16}$ or —NH—C(O)$R^{16}$ as defined above, or has one of the meanings given for $R^2$, and $R^{19}$ and $R^{20}$ each independently represent alkyl having 1-6 carbon atoms, or a radical of the formula III, and, in addition, $R^3$ represents, in the case where n is 2, a direct bond, alkylene having 1-20 carbon atoms, alkylene having 2-20 carbon atoms, which is interrupted by one or two of the members —O—, —S—, —SO—, —$SO_2$— or —CO—O—, arylene-bis-alkylene having 8-14 carbon atoms, alkenylene having 4-8 carbon atoms, or alkynylene having 4-8 carbon atoms.

2. A compound according to claim 1 wherein $R_a$, $R_b$, $R_c$, $R_d$ are methyl, and $R_e$ and $R_f$ are hydrogen.

3. A compound according to claim 1 wherein X is —O— or —NH—, $R^1$ is hydrogen, —O·, —OH, alkyl having 1-4 carbon atoms, allyl, propargyl, acetyl, acryloyl or crotonyl, $R^2$ is a hydroxybenzyl group of the formula IIa or IIb

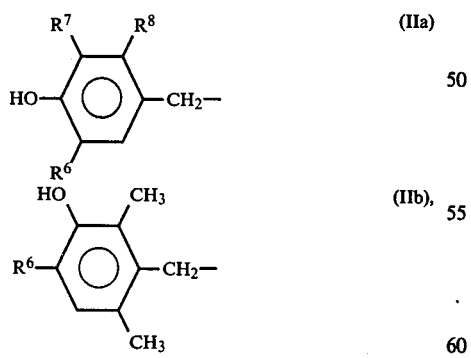

$R^6$ and $R^7$ each independently represent alkyl having 1-4 carbon atoms, $R^8$ represents hydrogen or methyl, $R^3$ represents in the case where n is 1 alkyl having 1-18 carbon atoms, alkyl having 1-4 carbon atoms which is substituted by one or two of the groups —CN, —C(O)—$YR^{12}$, —O—C(O)$R^{13}$ or —P(O)-(O$R^{14}$)$_2$, wherein Y is —O— or —NH—, $R^{12}$ is alkyl having 1-4 carbon atoms, or a group of the formula IIIb

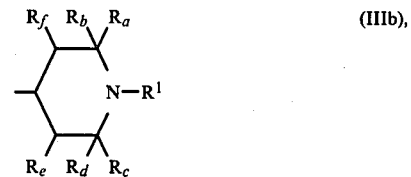

$R^{13}$ can be alkyl having 1-17 carbon atoms, cyclohexyl, phenyl or benzyl, and $R^{14}$ can be alkyl having 1-4 carbon atoms or allyl, and $R^3$ further represents alkyl having 2-18 carbon atoms which is interrupted by —O— or —S—, cycloalkyl having 5-12 carbon atoms, alkylcycloalkyl having 6-18 carbon atoms, alkenyl having 3-6 carbon atoms, alkynyl having 3-6 carbon atoms, phenyl, aralkyl having 7-15 carbon atoms, or a group —$OR^{15}$, wherein $R^{15}$ represents alkyl having 1-12 carbon atoms, allyl, propargyl or benzyl, or a group —O—$COR^{16}$ or —NH—$COR^{16}$, wherein $R^{16}$ represents alkyl having 1-12 carbon atoms, phenyl, 3,5-di-tert.butyl-4-hydroxyphenyl, or 2-(3,5-di-tert-.butyl-4-hydroxyphenyl)-ethyl, or a group of the formula IIIb, or in the case where n is 2, $R^3$ represents a direct bond, alkylene having 1-12 carbon atoms which can be interrupted by one or two of the groups —O—, —S— or —CO—O—, arylene-bis-alkylene having 8-14 carbon atoms or alkenylene having 4-8 carbon atoms.

4. A member of the group consisting of a compound of the formula Ia

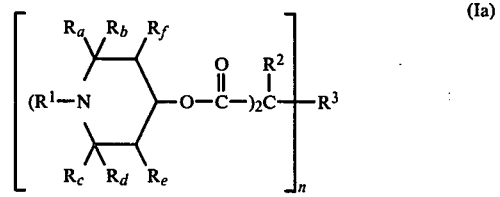

and an acid addition salt thereof, wherein n is 1 or 2, $R_a$ represents alkyl having 1-6 carbon atoms, $R_b$ represents alkyl having 1-6 carbon atoms, $R_c$ represents alkyl having 1-9 carbon atoms, phenyl benzyl or phenylethyl, $R_d$ represents alkyl having 1-6 carbon atoms, or $R_c$ and $R_d$ together represent tetra- or pentamethylene, $R_e$ represents hydrogen, alkyl having 1-5 carbon atoms, alkenyl or alkynyl having 3-4 carbon atoms or aralkyl having 7-8 carbon atoms, $R_f$ represents hydrogen, alkyl having 1-5 carbon atoms, alkenyl or alkynyl having 3-4 carbon atoms, or aralkyl having 7-8 carbon atoms, with $R_e$ and $R_f$ being mutually exchangeable, and $R^1$ represents hydrogen, —O·, —OH, alkyl having 1-12 carbon atoms, alkenyl having 3 or 4 carbon atoms, propargyl, benzyl or a group of the formula —$CH_2$—CH(O$R^5$)—$R^4$ wherein $R^4$ represents hydrogen, methyl or phenyl, and $R^5$ represents hydrogen or a group A—CO—, or $R^1$ represents a group A—CO—, and in both cases A represents alkyl having 1–12 carbon atoms, alkenyl having 2 or 3 carbon atoms, cyclohexyl, phenyl, benzyl, a phenyl or phenylethyl group substituted by 2 alkyl groups each having 1–4 carbon atoms and a hydroxyl group, alkylamino having 1–12 carbon atoms, dialkylamino having 2–16 carbon atoms, anilino, alkoxy having 1–12 carbon atoms, benzyloxy or phenoxy, $R^2$ represents a hydroxybenzyl group of the formula II

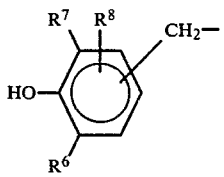

(II)

wherein $R^6$ and $R^7$ each independently represent an alkyl group having 1–9 carbon atoms, aralkyl having 7–9 carbon atoms or cycloalkyl having 5–8 carbon atoms, and $R^8$ represents hydrogen or methyl, and $R^3$ represents, in the case where n is 1, alkyl having 1–20 carbon atoms, or alkyl having 1–10 carbon atoms, which is substituted by one of the groups —$OR^9$, —$SR^{10}$, —CO—$R^{11}$, —CN, —CO—$OR^{12}$, —O—$C(O)R^{13}$ or —$P(O)(OR^{14})_2$, wherein $R^9$ denotes phenyl or alkylphenyl having 7–10 carbon atoms, benzyl or cyclohexyl, $R^{10}$ represents phenyl or alkylphenyl having 7–10 carbon atoms, $R^{11}$ denotes alkyl having 1–12 carbon atoms, $R^{12}$ denotes having 1–18 carbon atoms, cycloalkyl having 5–12 carbon atoms, or a group of the formula IIIb

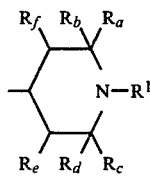

(IIIb)

$R^{13}$ denotes alkyl having 1–17 carbon atoms, cycloalkyl having 5–12 carbon atoms, or phenyl or phenylalkyl having 7–9 carbon atoms, wherein the phenyl radical is unsubstituted or substituted by at least one of the groups alkyl having 1–4 carbon atoms and hydroxyl, and $R^{14}$ denotes alkyl having 1–8 carbon atoms, allyl or phenyl, and $R^3$ further represents an alkyl group having 2–22 carbon atoms, which is interrupted by —O—, —S—, —SO— or —$SO_2$—, alkenyl having 3–18 carbon atoms, alkynyl having 3–8 carbon atoms, cycloalkyl having 5–12 carbon atoms, alkylcycloalkyl having 6–18 carbon atoms, cycloalkylalkyl having 6–14 carbon atoms, aralkyl or alkylaralkyl having 7–19 carbon atoms, or phenyl, and, in addition $R^3$ represents, in the case where n is 2, a direct bond, alkylene having 1–20 carbon atoms, alkylene having 2–20 carbon atoms, which is interrupted by one or two of the members —O—, —S—, —SO—, —$SO_2$— or —CO—O—, arylene-bis-alkylene having 8–14 carbon atoms, alkenylene having 4–8 carbon atoms, or alkynylene having 4–8 carbon atoms.

5. A member selected from the group consisting of a compound of the formula VIII

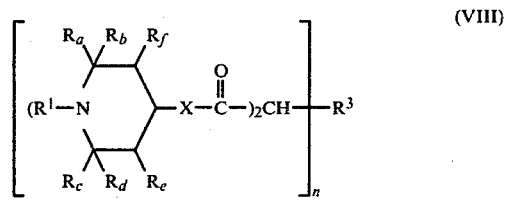

(VIII)

and an acid addition salt thereof, wherein
n is 1 or 2,
$R_a$ represents alkyl having 1–6 carbon atoms,
$R_b$ represents alkyl having 1–6 carbon atoms,
$R_c$ represents alkyl having 1–9 carbon atoms, phenyl, benzyl or phenylethyl,
$R_d$ represents alkyl having 1–6 carbon atoms, or
$R_c$ and $R_d$ together represent tetra- or pentamethylene,
$R_e$ represents hydrogen, alkyl having 1–5 carbon atoms, alkenyl having 3–4 carbon atoms, alkynyl having 3–4 carbon atoms or aralkyl having 7–8 carbon atoms,
$R_f$ represents hydrogen, alkyl having 1–5 carbon atoms, alkenyl having 3–4 carbon atoms or aralkyl having 7–8 carbon atoms, with $R_e$ and $R_f$ being mutually exchangeable, and
X represents oxygen or —NR—,
R represents hydrogen, alkyl having 1–18 carbon atoms, alkenyl having 3–4 carbon atoms, alkynyl having 3–4 carbon atoms, cycloalkyl having 5–12 carbon atoms, aryl having 6–10 carbon atoms, or aralkyl having 7–9 carbon atoms,
$R^1$ represents hydrogen, —O; —OH, alkyl having 1–12 carbon atoms, alkenyl having 3 or 4 carbon atoms, propargyl, benzyl or a group of the formula —$CH_2$—$CH(OR^5)$—$R^4$ wherein $R^4$ represents hydrogen, methyl or phenyl, and $R^5$ represents hydrogen or a group A—CO—, or $R^1$ represents a group A—CO—, and in both cases A represents alkyl having 1–12 carbon atoms, alkenyl having 2 or 3 carbon atoms, cyclohexyl, phenyl, benzyl, a phenyl or phenylethyl group substituted by 2 alkyl groups each having 1–4 carbon atoms and a hydroxyl group, alkylamino having 1–12 carbon atoms, dialkylamino having 2–16 carbon atoms, anilino, alkoxy having 1–12 carbon atoms, benzyloxy or phenoxy, $R^3$ represents, in the case where n is 1, alkyl having 1–20 carbon atoms, or alkyl having 1–10 carbon atoms, which is substituted by one or more of the groups —$OR^9$, —$SR^{10}$, —CO—$R^{11}$, —CN, —C(O)—$YR^{12}$, —O—$C(O)R^{13}$ or —$P(O)(OR^{14})_2$, wherein $R^9$ denotes phenyl or alkylphenyl having 6–10 carbon atoms, benzyl or cyclohexyl,
$R^{10}$ represents phenyl or alkylphenyl having 6–10 carbon atoms,
$R^{11}$ denotes alkyl having 1–12 carbon atoms, Y represents —O— or —NR— wherein R is as previously defined, $R^{12}$ denotes alkyl having 1-18 carbon atoms, cycloalkyl having 5-12 carbon atoms, or a group of the formula IIIb

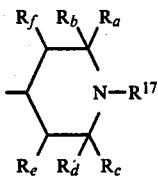
(IIIb), wherein $R^{17}$ represents a group as defined for R',
$R^{13}$ denotes alkyl having 1-17 carbon atoms, cycloalkyl having 5-12 carbon atoms, or phenyl or phenylalkyl having 7-9 carbon atoms, wherein the phenyl radical is unsubstituted or is substituted by at least one of the groups alkyl having 1-4 carbon atoms and hydroxyl, and
$R^{14}$ denotes alkyl having 1-8 carbon atoms, allyl or phenyl, and X has the above-defined meaning, and
$R^3$ further represents an alkyl group having 2-22 carbon atoms, which is interrupted by —O—, —S—, —SO— or —SO$_2$—, alkenyl having 3-18 carbon atoms, alkynyl having 3-8 carbon atoms, cycloalkyl having 5-12 carbon atoms, alkylcycloalkyl having 6-18 carbon atoms, cycloalkylalkyl having 6-14 carbon atoms, aralkyl or alkylaralkyl having 7-19 carbon atoms, phenyl, or a group —OR$^{15}$, wherein $R^{15}$ is alkyl having 1-18 carbon atoms, alkenyl having 3-4 carbon atoms, alkynyl having 3-4 carbon atoms, cycloalkyl having 5-12 carbon atoms or aralkyl having 7-9 carbon atoms, or $R^3$ represents a group —O—C(O)R$^{16}$ or —NH—C(O)R$^{16}$, wherein $R^{16}$ is alkyl having 1-12 carbon atoms, alkenyl having 2 or 3 carbon atoms, cyclohexyl, phenyl, benzyl, a phenyl or phenylethyl group substituted by 2 alkyl groups each having 1-4 carbon atoms and a hydroxyl group, or $R^3$ is a group of the formula III or of the formula IV

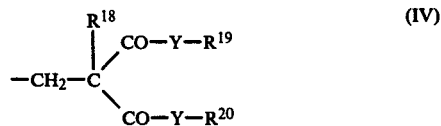
(IV)

wherein $R^{18}$ represents alkyl having 1-20 carbon atoms, allyl, benzyl, phenyl, cyclohexyl, alkoxyalkyl having 3-8 carbon atoms, or a group —O—C(O)R$^{16}$ or —NH—C(O)R$^{16}$ as defined above, or has one of the meanings given for R$^2$, and $R^{19}$ and $R^{20}$ each independently represent alkyl having 1-6 carbon atoms, or a radical of the formula III, and, in addition, $R^3$ represents, in the case where n is 2, a direct bond, alkylene having 1-20 carbon atoms, alkylene having 2-20 carbon atoms, which is interrupted by one or two of the members —O—, —S—, —SO—, —SO$_2$— or —CO—O—, arylene-bis-alkylene having 8-14 carbon atoms, alkenylene having 4-8 carbon atoms, or alkynylene having 4-8 carbon atoms.

6. A compound according to claim 1, said compound being butyl-(3,5-di-tert. butyl-4-hydroxybenzyl)-malonic acid-bis-(1,2,2,6,6-pentamethyl-4-piperidinyl)ester.

7. A compound according to claim 1, said compound being dodecyl-(3,5-di-tert.butyl-4-hydroxybenzyl)-malonic acid-bis-(1,2,2,6,6-pentamethyl-4-piperidinyl)ester.

8. A compound according to claim 1, said compound being 1,2,2,6,6-pentamethyl-4-piperidinyloxycarbonyl-methyl-(3,5-di-tert.butyl-4-hydroxybenzyl)-malonic acid-bis-(1,2,2,6,6-pentamethyl-4-piperidinyl)ester.

9. A compound according to claim 1, said compound being butyl-(3,5-di-tert.butyl-4-hydroxybenzyl)-malonic acid-bis-(2,3,6-trimethyl-2,6-diethyl-4-piperidinyl)ester.

10. A method for stabilizing plastics to protect them from damage caused by the action of oxygen, heat and light, characterized in that 0.01 to 5 percent by weight of a compound or salt thereof according to claim 1 is added to the plastics material.

11. A method according to claim 10 characterized in that 0.05 to 1.5 percent by weight of a compound according to claim 2 is added to the plastics material.

12. A method according to claim 10 characterized in that 0.1 to 0.8 percent by weight of a compound according to claim 3 is added to the plastics material.

13. A method according to claim 10 characterized in that 0.01 to 5 percent by weight of a compound according to claim 4 is added to the plastics material.

14. A plastics material stabilized against damage caused by the action of oxygen, heat and light, which plastics material contains as stabilizer 0.01 to 5 percent by weight of a compound or salt thereof according to claim 1.

15. A stabilized plastics material according to claim 14 characterized in that the material is a polyolefin, a styrene polymer or a polyurethane.

16. A method for stabilizing plastics, characterized in that 0.01 to 5 percent by weight of a compound according to claim 5 is added to the plastics material.

17. A stabilized plastics material containing 0.01 to 5 percent by weight of a compound according to claim 5.

18. A compound according to claim 1 wherein $R_a$ and $R_c$ are ethyl; $R_b$, $R_d$ and $R_e$ are methyl; and $R_f$ is hydrogen.

19. A compound according to claim 1 wherein n is 1 or 2; $R_a$, $R_b$, $R_c$ and $R_d$ are methyl and $R_e$ and $R_f$ are hydrogen, X is oxygen, $R^1$ is hydrogen, —O; alkyl having 1-4 carbon atoms, allyl or acetyl, $R^2$ is a hydroxybenzyl group of the formula (IIa) or (IIb),

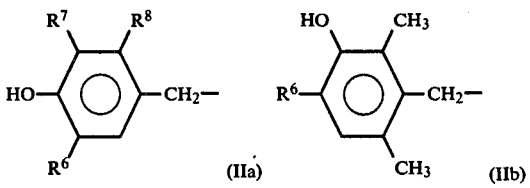

wherein $R^6$ represents tert. butyl, $R^7$ represents methyl or tert. butyl and $R^8$ represents hydrogen or methyl, and $R^3$ represents alkyl of 1-18 carbon atoms which is substituted by one or two groups of the formula —C(O)—OR$^{12}$ wherein $R^{12}$ represents alkyl of 1 to 4 carbon atoms or a group of the formula (IIIa)

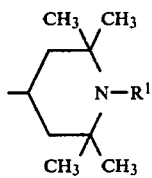

or a group —P(O)(OR$^{14}$)$_2$, wherein R$^{13}$ represents alkyl of 1-4 carbon atoms or R$^3$ represents allyl, propargyl, benzyl, phenyl, alkylene having 1-8 carbon atoms or xylylene.

20. A compound according to claim 5 wherein $R_a$, $R_b$, $R_c$ and $R_d$ are methyl and $R_e$ and $R_f$ are hydrogen.

21. A plastics material stabilized against damage caused by the action of oxygen, heat and light, which plastics material contains as stabilizer 0.01 to 5% by weight of a compound or salt thereof according to claim 4.

* * * * *